United States Patent
Schwartz et al.

(10) Patent No.: US 9,056,154 B2
(45) Date of Patent: Jun. 16, 2015

(54) HIGH-YIELD ACTIVATION OF POLYMER SURFACES FOR COVALENT ATTACHMENT OF MOLECULES

(75) Inventors: Jeffrey Schwartz, Princeton, NJ (US); T. Joseph Dennes, Cranbury, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 344 days.

(21) Appl. No.: 12/939,736

(22) Filed: Nov. 4, 2010

(65) Prior Publication Data

US 2011/0110986 A1 May 12, 2011

Related U.S. Application Data

(63) Continuation of application No. 11/677,576, filed on Feb. 21, 2007, now abandoned.

(60) Provisional application No. 60/775,127, filed on Feb. 21, 2006, provisional application No. 60/804,633, filed on Jun. 13, 2006.

(51) Int. Cl.
*A61L 31/08* (2006.01)
*A61L 27/30* (2006.01)
*C08J 7/04* (2006.01)
*A61L 27/14* (2006.01)
*A61L 27/28* (2006.01)
*A61L 27/38* (2006.01)
*A61L 27/50* (2006.01)
*A61L 31/00* (2006.01)
*C08H 1/06* (2006.01)
*C09J 189/04* (2006.01)

(52) U.S. Cl.
CPC .............. *A61L 31/082* (2013.01); *A61L 27/14* (2013.01); *A61L 27/28* (2013.01); *A61L 27/30* (2013.01); *A61L 27/38* (2013.01); *A61L 27/50* (2013.01); *A61L 31/005* (2013.01); *C08H 1/06* (2013.01); *C08J 7/04* (2013.01); *C08J 7/045* (2013.01); *C09J 189/04* (2013.01); *C08J 2379/02* (2013.01)

(58) Field of Classification Search
None
See application file for complete search history.

(56) References Cited

U.S. PATENT DOCUMENTS

| | | | |
|---|---|---|---|
| 4,746,366 A * | 5/1988 | Philipp et al. ............ | 106/287.19 |
| 6,103,255 A | 8/2000 | Levene et al. | |
| 6,146,767 A * | 11/2000 | Schwartz ...................... | 428/457 |
| 6,645,644 B1 | 11/2003 | Schwartz et al. | |
| 6,662,805 B2 | 12/2003 | Frondoza et al. | |
| 7,815,963 B2 * | 10/2010 | Schwartz et al. ............ | 427/2.26 |
| 2004/0001959 A1 * | 1/2004 | Schwartz et al. ............ | 428/469 |
| 2004/0023048 A1 * | 2/2004 | Schwartz et al. .......... | 428/472.1 |
| 2004/0148002 A1 | 7/2004 | Cheng et al. | |
| 2008/0206443 A1 * | 8/2008 | Schwartz et al. ............ | 427/2.26 |
| 2009/0104474 A1 * | 4/2009 | Schwartz et al. ............ | 428/704 |
| 2010/0215643 A1 * | 8/2010 | Clevenger et al. ......... | 424/130.1 |
| 2011/0093082 A1 * | 4/2011 | Schwartz et al. .......... | 623/20.14 |
| 2012/0208758 A1 * | 8/2012 | Maher et al. ................. | 514/13.6 |

FOREIGN PATENT DOCUMENTS

| JP | 08-295848 A | 11/1996 |
|---|---|---|
| JP | 2009-512551 A | 3/2009 |
| WO | 2007/050501 A2 | 5/2007 |

OTHER PUBLICATIONS

Kaim, W. and Schwederski, B., Bioinorganic Chemistry: Inorganic Elements in the Chemistry of Life, John Wiley & Sons LLC, 1994, Chapter 15.3.1, pp. 309-312.*
Ignatius, M.J. et al "Bioactive Surface Coatings for Nanoscale Instruments: Effects on CNS Neurons", J Biomed. Mater. Res., 1998,40(2), pp. 264-274.*
Bradley, D.C. "Metal Alkoxides as Precursors for Electronic and Ceramic Materials" Chem. Rev. 1989, 89(6), pp. 1317-1322.*
VanderKam, S.K. "Zirconium Alkoxide Interfaces for Adhesion Enhancement and Electrocatalysis" Thesis (Ph.D.), Princeton University, Jun. 1999, pp. 1-130.*
Balas, F et al "Surface modification of organic polymers with bioactive titanium oxide without the aid of a silane-coupling agent" J Mater Sci: Mater Med, 2007, 18, 1167-1174.*
Samha, et al., Langmuir-Blodgett Films of Pt(II) complexes, Langmuir (1992); vol. 8, No. 8, pp. 2001-2004.
Miller, et al., "Reaction between Tetra-tert-butoxyzirconium and Al(110)-OH in UHV," JACS (1995) vol. 117, No. 14, pp. 4037-40441.
Dennes, et al., "A nanoscale adhesion layer to promote cell attachment on PEEK," JACS (2009), vol. 131, No. 10, pp. 3456-3457 and S1-S5.
Dennes, et al., "Controlling cell adhesion on polyurethanes," Soft Matter (2008), vol. 4, No. 1, pp. 86-89.
Dennes, et al., "High-yield activation of scaffold polymer surfaces to attach cell adhesion molecules," JACS (2007), vol. 129, No. 1, pp. 96-97.

* cited by examiner

*Primary Examiner* — Jon P Weber
*Assistant Examiner* — Aaron J Kosar
(74) *Attorney, Agent, or Firm* — Fox Rothschild LLP; Peter J. Butch III; Robert N. Henrie, II

(57) ABSTRACT

Polymer surfaces coated with organometallic layers, wherein the organometallic layers and polymer surfaces have functional groups that react to bond the organometallic layer to the polymer surface with organometallic functional groups remaining unreacted for the subsequent covalent attachment of organic overlayers. Coating methods and coated articles are also disclosed.

27 Claims, 2 Drawing Sheets

X = RGD ; 7a
X = Dansyl-Cys ; 7b

X = RGD ; 9a
X = Dansyl-Cys ; 9b

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: integrin binding sequence

<400> SEQUENCE: 1

Arg Gly Asp Cys
1

<210> SEQ ID NO 2
<211> LENGTH: 7
<212> TYPE: PRT
<213> ORGANISM: Artificial Sequence
<220> FEATURE:
<223> OTHER INFORMATION: anti-staphylococcal agent
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2

Tyr Ser Pro Xaa Thr Asn Phe
1               5

<210> SEQ ID NO 3
<211> LENGTH: 7
<212> TYPE: PRT
<213> ORGANISM: Artificial Sequence
<220> FEATURE:
<223> OTHER INFORMATION: anti-staphylococcal agent

<400> SEQUENCE: 3

Tyr Ser Pro Trp Thr Asn Phe
1               5

<210> SEQ ID NO 4
<211> LENGTH: 7
<212> TYPE: PRT
<213> ORGANISM: Artificial Sequence
```

<220> FEATURE:
<223> OTHER INFORMATION: anti-staphylococcal agent
<220> FEATURE:
<221> NAME/KEY: MISC_FEATURE
<222> LOCATION: (7)..(7)
<223> OTHER INFORMATION: -NH2

<400> SEQUENCE: 4

Tyr Ser Pro Trp Thr Asn Phe
1               5

<210> SEQ ID NO 5
<211> LENGTH: 504
<212> TYPE: DNA
<213> ORGANISM: Staphylococcus aureus

<400> SEQUENCE: 5
atgaagaaac tatatacatc ttatggcact tatggatttt tacatcagat aaaaatcaat      60
aacccgaccc atcaactatt ccaattttca gcatcagata cttcagttat ttttgaagaa     120
actgatggtg agactgtttt aaaatcacct tcaatatatg aagttattaa agaaattggt     180
gaattcagtg aacatcattt ctattgtgca atcttcattc catcaacaga agatcatgca     240
tatcaacttg aaaagaaact gattagtgta acgataatt tcagaaactt tggtggcttt      300
aaaagctatc gtttgttaag acctgctaaa ggtacaacat acaaaattta tttcggattt     360
gctgatcgac atgcatacga agactttaag caatctgatg cctttaatga ccattttca      420 aaagacgcat taagtcatta ctttggttca agcggacaac attcaagtta ttttgaaaga     480
tatctatacc caataaaaga atag                                             504

<210> SEQ ID NO 6
<211> LENGTH: 834
<212> TYPE: DNA
<213> ORGANISM: Staphylococcus aureus

<400> SEQUENCE: 6
atggctatta aaagtataa gccaataaca atggtcgtc gtaatatgac ttcgttagat        60
ttcgcagaaa tcacgaaaac tacacctgaa aagtcattat taaaaccgct accgaaaaaa    120
gcgggacgta caaccaagg taaattgact gtaagacacc atggtggtgg acacaaacgt     180
caataccgtg ttatcgattt caaacgtaac aaagatggta tcaatgcaaa agttgattct    240
attcaatatg atccaaaccg ctcagcaaac atcgctttag ttgtatatgc agacggtgaa    300
aaacgatata tcattgctcc taaggatta gaagtaggtc aaatcgttga agtggtgct      360 gaagctgaca tcaaagttgg taacgcatta ccattacaaa acattccagt tggtacagta    420
gtacacaaca tcgagcttaa acctggtaaa ggtggacaaa tcgctcgttc agctggtgca    480
agtgctcaag tacttggtaa agaaggtaaa tacgtattaa tcagattaag atctggtgaa    540
gttcgtatga tcttatctac ttgccgtgct acaatcggtc aagttggtaa cctacaacac    600
gaattagtta acgttggtaa agccggacgt tcaagatgga aggtatccg tccaacagtt     660 cgtggttctg taatgaaccc taacgatcac ccacacggtg gtggtgaagg tcgtgctcct    720
atcggtagac catctccaat gtcaccatgg ggtaaaccta cgcttggtaa gaaaactcgt    780
cgtggtaaaa aatcatcaga caaacttatc gttcgtggac gtaagaaaaa ataa           834

<210> SEQ ID NO 7
<211> LENGTH: 46
<212> TYPE: PRT
<213> ORGANISM: Staphylococcus aureus

```
<220> FEATURE:
<221> NAME/KEY: mat_peptide
<222> LOCATION: (25)..(33)
<223> OTHER INFORMATION: Agr autoinducing peptide

<400> SEQUENCE: 7

Met Asn Thr Leu Tyr Lys Ser Phe Phe Asp Phe Ile Thr Gly Val Leu
                -20             -15                 -10
Lys Asn Ile Gly Asn Val Ala Ser Tyr Ser Thr Cys Tyr Phe Ile Met
             -5           -1   1              5
Asp Glu Val Glu Ile Pro Lys Glu Leu Thr Gln Leu His Glu
     10              15              20
```

HIGH-YIELD ACTIVATION OF POLYMER SURFACES FOR COVALENT ATTACHMENT OF MOLECULES

CROSS-REFERENCE TO RELATED APPLICATIONS

The present application is a continuation of U.S. application Ser. No. 11/677,576, filed Feb. 21, 2007 now abandoned, which in turn claims priority benefit under 35 U.S.C. §119(e) of U.S. Provisional Patent Application No. 60/775,127, filed Feb. 21, 2006, and 60/804,633, filed Jun. 13, 2006. The disclosures of both applications are incorporated herein by reference.

STATEMENT REGARDING FEDERALLY FUNDED RESEARCH

This invention was made with government support under Grant No. CHE-0310178 awarded by the National Science Foundation. The U.S. government has certain rights in this invention.

BACKGROUND OF THE INVENTION

The present invention relates to covalently binding organic materials to the surfaces of polymer substrates by functionalizing the surfaces with linker moieties containing transition metal complexes. In particular, the present invention relates to modifying polymer surfaces with organometallic compounds that have functional groups that react with functional groups of the polymer surface. The modified polymer surface can be further reacted with a compound, polymer or oligomer that contains functional groups that are reactive with functional groups of the organometallic compound that remain after reaction with the polymer surface. The present invention further relates to functionalizing polymer surfaces to support cell growth and the attachment of biologically active molecules and other compounds of interest.

Bioactive polymeric scaffolds are of increasing importance for use in tissue regeneration in a variety of clinical applications, and a scaffold that supports cell growth is a critical first step in such regeneration. Surface wetting properties of many polymers used as bioscaffolds are not conducive to biointegration, but incorporation of surface functional groups can effect substantial changes in a polymer's wettability while generating reactive sites suitable for attachment of peptides and other biomolecules.

Adjustment of the surface properties of polymers such as those from which preformed polymeric therapeutic devices are formed, has proven problematic because those polymers most often used as biomaterials are resistant to specific surface treatments. To circumvent this problem, polymer scaffold materials have been prepared by blending, copolymerization, or physical treatment, but these methods can result in alteration of the bulk properties of the polymer. Furthermore, these methods or attempts to surface modify pre-cast polymers using standard methods of organic synthesis, result only in low surface coverage by peptides that do not approach those that can be achieved on metallic substrates.

Surface modification has also proven problematic in other areas of polymer and polymer surface customization. There is a need to modify polymer surfaces so as to change the surface characteristics of the polymer surface without changing the bulk properties of the polymer. More particularly, there remains a need for polymer surfaces that support cell growth as well as the attachment of biologically active molecules and other compounds of interest.

SUMMARY OF THE INVENTION

The present invention relates to a coated substrate having a polymer surface and an organometallic coating layer formed thereon. The organometallic coating and polymer surface have co-reactive functional groups that are reacted to bond the coating to the surface. Preferably, the organometallic coating has remaining unreacted functional groups that are reacted with co-reactive functional groups of a subsequently applied compound, oligomer or polymer.

In another embodiment, the present invention relates to a method of coating a polymer surface, which includes coating an organometallic compound on the polymer surface, wherein the polymer surface and the organometallic coating have co-reactive functional groups; and reacting the functional groups of the organometallic compound with the co-reactive functional groups of the polymer surface to form an organometallic coating on the polymer surface. Preferably, a compound, oligomer or polymer containing functional groups that react with the remaining unreacted functional groups of the organometallic compound is applied to the organometallic layer and the functional groups of the compound, oligomer or polymer are reacted with the remaining functional groups in the organometallic layer to form an organic coating on the organometallic coating.

In one embodiment, the present invention provides a novel approach to polymer surface modification that enables high surface density derivatization of polymers with reactive surface moieties containing acidic covalent bonds. The polymers need not contain pendant functional groups with acidic covalent bonds. For example, polymers with exposed amide functionality contain acidic N—H bonds, which can serve as sites for chemical derivatization when appropriately activated. In particular, coordination of the carbonyl Group to an appropriate metallic center further acidifies the N—H bonds and facilitates derivatization. In addition, acidic C—H bonds on polymer surfaces can also serve as sites for chemical derivatization when appropriately activated. In particular, coordination of the carbonyl Group to an appropriate metallic center further acidifies the CH bonds and facilitates derivatization.

Therefore, according to one aspect of the present invention, a coated substrate is provided having a polymer surface with exposed reactive functional groups containing acidic covalent bonds and an organometallic coating layer formed thereon and covalently bonded thereto, wherein the organometallic coating layer contains transition metal atoms selected from atoms of Group 4, Group 5 and Group 6 of the Periodic Chart that have been covalently bonded to the polymer surface by reaction of a polyalkoxide or polydialkylamide of the transition metal with the reactive functional groups exposed on the polymer surface. Zirconium and titanium are two examples of such transition metals. Examples of reactive functional groups with acidic covalent bonds include, but are not limited to, hydroxyl groups, phenol groups, amide N—H groups, amino groups, imide groups, urethane groups, urea groups, thiol groups, carboxylic acid groups, carboxylic acid ester groups, carboxylic acid amide groups, sulfonic acid groups, acidic C—H groups, and the like. Each of these groups will covalently bond the organometallic coating layers.

The organometallic layer can then be further bonded to organic groups or ligands of interest that are reactive with the organometallic layer, thereby attaching covalently the organic ligands of interest to the polymer surface. Therefore, according to another aspect of the present invention, a coated substrate is provided having a polymer surface with an organometallic coating layer formed thereon and covalently bonded thereto, wherein the organometallic coating layer contains transition metal atoms selected from atoms of Group 4, Group 5 and Group 6 of the Periodic Chart which have been covalently bonded to the polymer surface by reaction of a polyalkoxide or polydialkylamide of the transition metal with the reactive functional groups on the polymer surface, wherein each transition metal atom additionally has covalently bonded to it one or more organic ligands.

The present invention provides coated substrates in which up to 40%, up to 60%, up to 75% or up to 100% of the polymer surface has organic groups or ligands bonded thereto. This is accomplished without changing the bulk material properties of the substrate. The percentage of the polymer surface with organic ligands bonded thereto depends on relationship between the size of the organic ligand and the size of the metal complex used to bond the organic ligand to the polymer and is readily apparent to one of ordinary skill in the art guided by the present specification.

The present invention thus provides a novel type of interface that enables strong adhesion between a polymer surface and an organic coating. The coating modifies the surface of the polymer making it more hydrophilic or hydrophobic as may be desired. The modification can make the polymer surface more or less receptive to subsequently applied coatings, improving or minimizing the adhesion of the polymer to the subsequently applied coating. The polymer surface can be a polymer coating on an article made from another material, such as glass, silicon dioxide, metal, or another polymer. The polymer surface can also be the surface of a pre-cast polymer article. Examples of suitable polymers with reactive functional groups include polyamides, such as nylon, silk, and collagen, polyacrylamides, polyimides, polyurethanes, polyureas, polysulfonamides, polyesters, polysaccharides, such as haluronic acid, methylcellulose and proteoglycans, and the like, and copolymers of any of these polymers.

According to one embodiment of this aspect of the invention, the polymer is a biocompatible polymer and the polymer-coated or polymer-cast article is a medical implant or biological scaffold or porous matrix. The organic ligand can then be a protein, peptide, peptide mimetic, small molecule ligand for a cell surface receptor, or other biologically or pharmaceutically active compound having utility as a coating on a medical implant. The organic ligand can thus promote or prevent cell growth or proliferation, promote or discourage cell adhesion, prevent infection, or prevent or promote blood clotting or adhesion.

According to another embodiment of this aspect of the invention, the polymer is a fabric formed from a woven or non-woven fiber. The fiber can be a natural fiber with exposed functional groups, such as silk, wool, cotton, linen, collagen and the like. The fiber can also be a synthetic fiber with exposed functional groups, such as nylon.

The present invention also provides a method by which organic ligands or groups may be covalently bonded to polymer surfaces with reactive functional groups using an organometallic interface. Therefore, according to another aspect of the present invention, there is provided a method of forming an organic layer on a polymer surface with reactive functional groups, which method includes the steps of:

providing a substrate having a polymer surface covalently bonded to an organometallic surface layer of dialkylamides or alkoxides of transition metals selected from Group 4, Group 5 or Group 6 of the Periodic Chart, wherein the dialkylamides or alkoxides are bonded at the transition metal atoms to the polymer surface; and reacting the transition metal dialkylamide or alkoxide layer with an organic overlayer comprising a compound, oligomer or polymer capable of reacting with unreacted transition metal dialkylamide or alkoxide groups to covalently bond the organic compound, oligomer or polymer to the transition metals.

The polymer surface can be provided with the organometallic surface layer by reacting a polymer substrate having reactive functional groups with acidic covalent surface bonds with a polydialkylamide or polyalkoxide of the Group 4, Group 5 or Group 6 transition metal having two or more dialkylamide or alkoxide groups, so that an organometallic surface layer is formed, covalently bonded to the polymer surface, and having at least one unreacted dialkylamide or alkoxide group.

The method of the present invention thus provides high yield coatings on polymer surfaces with the adhesion properties of physical deposition methods under mild reaction conditions. In particular, the coatings of the present invention may be formed at ambient temperatures.

In addition to the coatings of the present invention and the method by which they are formed, the present invention also provides coated implantable medical devices, methods for improving cellular growth and attachment, tissue in-growth and adhesion to tissue for implantable medical devices using the coatings of the invention and the inventive coating methods, and methods for implanting medical devices by first coating them according to the present invention.

The invention can also be used to make the polymer surface electrically conductive, semi-conductive or electrically insulating making it useful in organic thin film transistors, light emitting devices and electrolytic capacitors.

Other features of the present invention will be pointed out in the following description that discloses, by way of example, the principles of the invention and the best methods which have been presently contemplated for carrying them out.

DETAILED DESCRIPTION OF PREFERRED EMBODIMENTS

Figure 1:
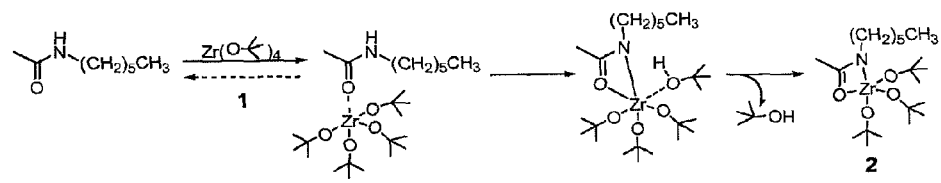
FIG. 1 depicts the reaction of N-hexylacetamide and zirconium tetra(tert-butoxide)

The coated substrates are formed by reacting a polymer surface having functional groups with acidic covalent bonds that are reactive with other functional groups, specifically transition metal polydialkylamides and polyalkoxides. For purposes of the present invention, "reactive groups" on a polymer surface are defined as functional group with acidic covalent bonds. Examples of suitable polymer surface reactive functional groups include those having a reactive N—H bond such as amine, amide, imide, urethane and urea groups. Examples of other reactive functional groups include hydroxyl, oxy, ether, thiol, carbonyl including keto, ester, free acid and acid anhydride, sulfonic acid and acidic —CH groups.

The polymer can be in the form of a molded article, a rigid or flexible film or a coating. Examples of suitable polymers containing these groups are polyamines such as polyoxyalkylene polyamines, polyethers such as polyethylene glycol, polyketones such as PEEK, polyamides such as nylon, polyacrylamides, polyimides, polyesters and polyurethanes such as the reaction product of polymeric polyols with polyisocyanates such as techoflex. The preferred functional groups are

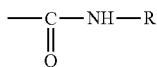

groups such as those associated with polyamides. Suitable polyamides include nylons such 15 as Nylon 6. Nylon 4/6, Nylon 6/6, Nylon 6/9, Nylon 6/10, Nylon 6/12, Nylon 12, Nylon 6/66, and the like.

The reactive functional groups containing acidic covalent bonds may be either pendant to or between monomeric repeating units of the polymer, a portion of which are exposed at the polymer surface.

The organometallic compound used in the practice of the invention is preferably derived from a metal or a metalloid such as selected from Group 3 of the Periodic Chart or a transition metal selected from Group 4, 5 and 6 of the Periodic Chart. Preferred metals are aluminum and transition metals are selected from Group 4 with titanium and zirconium being the most preferred. The organo portion of the organometallic compound contains functional groups that are reactive with the functional groups of the polymer surface. For purposes of the present invention, "organometallic" compounds are defined as including compounds that do not necessarily contain metal-carbon bonds. Examples of suitable organo groups of the organometallic compound are dialkylamide and alkoxide groups containing from 1 to 18, preferably 2 to 8 carbon atoms. Examples of alkoxide groups include ethoxide, propoxide, isopropoxide, butoxide, isobutoxide and tert-butoxide. Examples of dialkylamide groups include diethyl amide, dipropyl amide, diisopropyl amide, dibutyl amide, diisobutyl amide and ditert-butyl amide.

Reaction may be by transition metal coordination followed by proton transfer to a dialkylamide or alkoxide ligand and loss of an dialkylamine or alkanol, so that an organometallic layer covalently bonds with the polymer surface. The organometallic layer is believed to consist of a transition metal layer in which the dialkylamide or alkoxide groups of the transition metal are covalently bonded to the polymer at the reactive functional group, Depending upon the position of the transition metal on the Periodic Chart, the transition metal dialkylamide or alkoxide will have from two to six dialkylamide or alkoxide groups. Transition metal tetra-alkoxides and tetra-dialkylamides are preferred, with the most preferred transition metal tetra-alkoxide and tetra-dialkylamide being zirconium tetra tert-butoxide and zirconium tetra-diethylamide.

With Group 4 transition metal tetra-alkoxides and tetra-dialkylamides, at least one of the alkoxide or amide groups reacts with reactive functional groups on the polymer surface to form covalent bonds between the reactive functional groups and the transition metal. The reaction proceeds by proton transfer to a dialkylamide or alkoxide Group of a transition metal, producing an equivalent quantity of the corresponding dialkyl amine or alkanol. At least one dialkylamide or alkoxide Group does not react and remains available for subsequent reaction with the organic overlayer material.

Group 5 transition metals form pentaalkoxides or pentadialkylamides and oxotrialkoxides or oxotridialkylamides that are suitable for use with the present invention. These compounds can also react by proton transfer where possible to covalently bond the transition metal to the reactive functional group on the polymer surface, producing an equivalent quantity of an alkanol or dialkylamine and leaving at least one unreacted alkoxide or dialkylamide Group for subsequent reaction with organic overlayer material.

Group 6 transition metals form hexaalkoxides or hexadialkylamides, oxotetra alkoxides or oxotetradialkylamides and dioxo-dialkoxides or dioxodidialkylamides that are all suitable for use with the present invention. These compounds can also react by proton transfer where possible to covalently bond the transition metal to the reactive functional group on the polymer surface, producing an equivalent quantity of an alkanol or dialkylamine and leaving at least one unreacted alkoxide or dialkylamide Group for subsequent reaction with organic overlayer material.

Advantageously, many of the transition metal alkoxides dialkylamides suitable for use with the present invention are commercially available. This includes the preferred zirconium tetra (tert-butoxide) and zirconium tetra-diethylamide, which may be obtained from Strem. However, the transition metal alkoxides and dialkylamides may also be prepared by conventional techniques by reacting a halide or oxo-halide of the selected transition metal, depending on the desired number of alkoxide or dialkylamide groups, with the corresponding alkoxide or dialkylamide of a metal selected from Group 1 or Group 2 of the Periodic Chart.

With regard to the preferred metals titanium and zirconium, the alkoxides are titanates and zirconates. These compounds can be reactive simple esters, polymeric forms of the esters and chelates that are relatively stable. Examples of various compounds include a. alkyl ortho esters of titanium and zirconium having the general formula 25 $M(OR)_4$, wherein M is selected from Ti and Zr and R is $C_{1-18}$ alkyl, b. polymeric alkyl titanates and zirconates obtainable by condensation of the alkyl ortho esters of (a), i.e., partially hydrolyzed alkyl ortho esters of the general formula $RO[-M(OR)_2O-]_{x-1}R$, wherein M and R are as above and x is a positive integer, c. titanium chelates, derived from ortho titanic acid and polyfunctional alcohols containing one or more additional hydroxyl, keto, carboxyl or amino groups capable of donating electrons to titanium. These chelates have the general formula

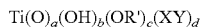

wherein a=4−b−c−d; b=4−a−c−d; c=4−a−b−d; d=4−a−b−c; R' is H, R as above or X—Y, wherein X is an electron donating group such as oxygen or nitrogen and Y is an aliphatic radical having a two or three carbon atom chain such as i. —CH$_2$CH$_2$—, e.g., of ethanolamine, diethanolamine and triethanolamine,

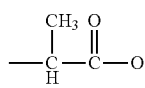

ii. e.g., of lactic acid,

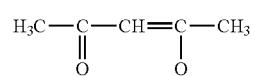

iii. e.g., of acetylacetone enol form, and

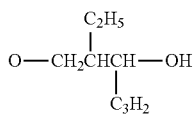

iv. e.g., as in 1,3-octyleneglycol d. titanium acylates having the general formula $Ti(OCOR)_{4-n}(OR)_n$ wherein R is $C_{1-18}$ alkyl as above and n is an integer of from 1 to 3, and polymeric forms thereof, and e. mixtures thereof.

The organometallic compound is usually dissolved or dispersed in a diluent. Examples of suitable diluents are alcohols such as methanol, ethanol and propanol, aliphatic hydrocarbons, such as hexane, isooctane and decane, ethers, for example, tetrahydrofuran and dialkylethers such as diethylether. Also, adjuvant materials may be present in the organometallic composition. Examples include surfactants and antistatic agents. The adjuvants if present are present in amounts of up to 30 percent by weight based on the non-volatile content of the composition.

The concentration of the organometallic compound in the composition is not particularly critical but is usually at least 1.0 micromolar, typically from about 1.0 micromolar to about 100 millimolar, and more typically from about 1.0 micromolar to about 50 millimolar.

The organometallic treating composition can be obtained by mixing all of the components at the same time with low shear mixing or by combining the ingredients in several steps. The organometallic compounds are reactive with moisture, and care should be taken that moisture is not introduced with the diluent or adjuvant materials and that mixing is conducted in a substantially anhydrous atmosphere.

The organometallic composition is applied to the polymer surface by conventional means such as dipping or spraying. The organometallic compound is then exposed to conditions sufficient to form a polymeric metal oxide coating preferably with unreacted dialkylamide or alkoxide and/or hydroxyl groups. This can be accomplished by depositing the film under conditions resulting in hydrolysis and self-condensation of the alkoxide or dialkylamide. These reactions result in a polymeric coating being formed that provides cohesive strength to the film. The conditions necessary for these reactions to occur is to deposit the film in the presence of water, such as a moisture-containing atmosphere. The resulting film preferably has some unreacted dialkylamide or alkoxide groups and/or hydroxyl groups for subsequent reaction and possible covalent bonding with reactive groups of an overlayer material. Concurrently with the self-condensation reaction, the diluent is evaporated. Depending on the reactivity of the functional groups in the organometallic compound and on the polymer surface, heating may be required to bond the organometallic layer to the substrate. For example, temperatures of about 50 to about 200° C. may be used. However, for readily co-reactive groups, ambient temperatures, that is, about 20° C., may be sufficient.

As mentioned above, an overlayer can be applied to the organometallic film. Such an overlayer material can be derived from a compound, oligomer or polymer that contains groups that are reactive with the dialkylamide or alkoxide and/or hydroxyl groups. Preferred overlayers are the layers of organic ligands of carboxylic and organophosphorus acids as generally described in U.S. Pat. No. 6,645,644, the disclosure of which is incorporated by reference. Certain organic components can also enhance the non-fouling characteristics of a surface so that cells (e.g., from bacteria, scar tissue, mildew, mold, and other unwanted organisms) do not adhere well to the treated surface.

Examples of organophosphorus acids or derivative thereof are organophosphoric acids, organophosphonic acids and/or organophosphinic acids including derivatives thereof. Examples of derivatives are materials that perform similarly as the acid precursors such as acid salts, acid esters and acid complexes. The organo group of the phosphorus acid may be a monomeric, oligomeric or polymeric group. Examples of monomeric phosphorus acids are phosphoric acids, phosphonic acids and phosphinic acids including derivatives thereof.

Examples of monomeric phosphoric acids are compounds or a mixture of compounds having the following structure:

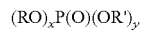

wherein x is 1-2, y is 1-2 and x+y=3, R is a radical having a total of 1-30, preferably 6-18 carbons, where R' is H, a metal such as an alkali metal, for example, sodium or potassium or lower alkyl having 1 to 4 carbons, such as methyl or ethyl. Preferably, for a portion of the phosphoric acid compounds in the overlayer, R' is H. The organic component of the phosphoric acid (R) can be a hydrocarbon and can be aliphatic (e.g., alkyl having 2-20, preferably 6-18 carbon atoms) including a saturated or unsaturated carbon chain (e.g., an olefin), unsubstituted or substituted aliphatic, such as fluoro-substituted, or can be aryl or aryl-substituted moiety. Substitution in the omega position is preferred.

Examples of monomeric phosphonic acids are compounds or mixture of compounds having the formula:

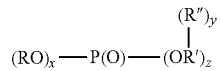

wherein x is 0-1, y is 1, z is 1-2 and x+y+z is 3. R and R" are each independently a radical having a total of 1-30, preferably 6-18 carbons. R' is H, a metal, such as an alkali metal, for example, sodium or potassium or lower alkyl having 1-4 carbons such as methyl or ethyl. Preferably, for at least a portion of the phosphonic acid compounds in the overlayer, R' is H. The organic component of the phosphonic acid (R and R") can be a hydrocarbon and can be aliphatic (e.g., alkyl having 2-20, preferably 6-18 carbon atoms) including a saturated or unsaturated carbon chain (e.g., an olefin), unsubstituted or substituted aliphatic such as fluoro-substituted, or can be an aryl or aryl-substituted moiety. Substitution in the omega position is preferred.

Examples of monomeric phosphinic acids are compounds or mixture of compounds having the formula:

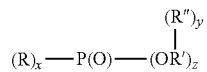

wherein x is 0-2, y is 0-2, z is 1 and x+y+z is 3. R and R" are each independently radicals having a total of 1-30, preferably 6-18 carbons. R' is H, a metal, such as an alkali metal, for example, sodium or potassium or lower alkyl having 1-4 carbons, such as methyl or ethyl. Preferably, for at least a portion of the phosphinic acid compounds in the overlayer, R' is H. The organic component of the phosphinic acid (R, R") can be a hydrocarbon and can be aliphatic (e.g., alkyl having 2-20, preferably 6-18 carbon atoms) including a saturated or unsaturated carbon chain (e.g., an olefin), an unsubstituted or substituted aliphatic such as fluoro-substituted, or can be an aryl or aryl-substituted moiety. Substitution in the omega position is preferred.

Examples of organo groups which may comprise R and R" include long and short chain aliphatic hydrocarbons, aromatic hydrocarbons and substituted aliphatic hydrocarbons and substituted aromatic hydrocarbons. Examples of substituents include carboxyl such as carboxylic acid, hydroxyl, amino, imino, amido, thio, cyano, and halo such as fluoro.

In addition to the organophosphorus acids mentioned above, oligomeric or polymeric organophosphorus acids resulting from self-condensation of the respective organophosphorus acid may be used.

The overlayer material can further include a suitable solvent. For example, for organophosphorus materials, solvents such as an alcohol (e.g., ethanol), tetrahydrofuran, dichloromethane, chloroform, 2:1 by volume ethanol:toluene, acetonitrile and water can be used. The concentration of the overlayer material can range from about 0.1 micromolar to as high as the upper limit of the solubility of the overlayer material in a specific solvent, for example, from about 0.1 micromolar to about 100 millimolar, from about 0.1 micromolar to about 10.0 millimolar, for example, about 1.0 millimolar.

The solution of the overlayer material can be applied to the organometallic coating using one or more techniques, and allowing the solution to evaporate. For example, the solution can be sprayed (e.g., a few microgram per square centimeter) onto, dropped on, and/or painted on the organometallic coating. Alternatively, the substrate with the organometallic coating can be dipped into the solution. The solution can be applied by doctor blade, reverse roll, die coater, wire bar, knife and blade coaters. Direct gravure, micro gravure and reverse gravure techniques can also be used. Suitable solvents include solvents in which the organic compound is soluble including aqueous buffer solutions, tetrahydrofuran, acetonitrile, methylene chloride, chloroform and water, and the like. The substrate will then be removed from the solution, rinsed with an inert solvent such as water, acetonitrile, methanol, tetrahydrofuran or the like and then dried to provide a substrate with a polymer surface having an organic ligand surface layer covalently attached thereto.

Besides the techniques mentioned above, the transition metal amide or alkoxide may be applied to the polymer surface by vapor deposition. Typically, an excess of transition metal amide or alkoxide is employed, and the reaction performed at ambient temperature. With vapor deposition, upon completion of the reaction, the vacuum should once again be maintained to remove excess transition metal alkoxide and alkanol byproduct.

Other methods of applying the solution to the organometallic coating are described in US 2004/0023048 and PCT/US/2003/034909, the disclosures of both of which are incorporated by reference. Application of the solution may be in one or multiple layers.

After the solution of the overlayer material is applied to the organometallic coating and the solvent is allowed to evaporate, the applied layer may optionally be treated to enhance bonding directly to the organometallic coating. The applied layer can be treated with heat and/or electromagnetic radiation, such as microwave radiation (e.g., 2450 MHz or a wavelength of about 12 cm). In some embodiments, the applied layer is exposed to radiant and/or induction heating, for example, to a temperature of 50° C. to about 200° C. (e.g., about 150° C.) for about 30-120 seconds. The heating time may be a function of the temperature used, and the temperature used may be restricted by design considerations and/or materials limitations.

In a similar aspect, the present invention can be looked at as bonding organic ligands or groups to substrates with polymer surfaces having functional groups, for example amide groups. For purposes of the present invention, "polymer surfaces having functional groups" are defined as polymers with functional groups either within or between monomeric repeating units, a portion of which are exposed at the polymer surface, either in the form of a coating or a molded article, and are reactive with the organometallic compound, for example, a transition metal. Reaction may be by transition metal coordination to the functional group. For an amide, this may be followed by N—H proton transfer to an alkoxide ligand and loss of an alkanol, so that an organometallic layer covalently bonds with the amide Group on the polymer surface.

Although not to be bound by any theory, it is believed the reaction of the transition metal complex with the polymer substrate proceeds by coordination of the metal to the functional group of the polymer. This may be followed by the transfer of a proton from the polymer functional to the ligand of the transition metal, forming the corresponding dialkylamine or alkanol and bonding the polymer functional group to the transition metal. In the case of vapor deposition techniques, once the reaction is complete, the vacuum is maintained in order to draw off any excess of the transition metal or dialkylamine or alkanol byproduct.

Further, although not to be bound by any theory, it is believed the reaction of the transition metal complex with the organic overlayer proceeds by coordination of the functional group on the organic overlayer to the transition metal. This may be followed by the transfer of a proton from the organic functional to the ligand of the transition metal, forming the corresponding dialkylamine or alkanol and bonding the organic overlayer to the transition metal.

The organic compound may also be selected from phosphoric acid and organophosphonic acids. For purposes of the present invention "phosphoric acid" is defined according to its well-understood meaning, $H_3PO_4$. "Organophosphonic acids" refers to compounds having the formula $H_2RPO_3$, wherein R is a hydrocarbon ligand with a carbon directly bonded to phosphorus.

Overlayers based on organophosphorus acids are covalently bonded as phosphate esters of the organometallic layer transition metal. The phosphate esters may be hydrolyzed to form transition metal polyphosphate coatings on the substrate surface. The phosphate and polyphosphate coatings are rich in hydroxyl groups that are available for further chemical modification.

The coated polymer substrates also include organic ligands or groups covalently bonded to the polymer surfaces. By reacting organic overlayer materials with the transition metal dialkylamide or alkoxide layer, organic ligands form as a layer on the polymer surface, covalently bonded at the transition metal to the polymer surface. The ability to react the organic overlayer material with the transition metal dialkylamide or alkoxide layer covalently bonded to the polymer surface at ambient temperature is particularly useful for the attachment of biologically active ligands such as peptides, proteins, or any other ligand which is deactivated under extreme conditions.

Examples of biologically active ligands that are covalently attached to the polymer surface of a substrate by an organometallic layer include integrins, integrin receptors, cell attachment mediators, such as peptides containing variations of the Arg-Gly-Asp integrin binding sequence known to enhance cellular attachment, and substances that enhance or exclude particular varieties of cellular or tissue ingrowth. Such substances include, for example, osteoinductive substances, such as bone morphogenic proteins (BMP), and substances that induce cellular growth, proliferation, and/or differentiation such as epidermal growth factor (EGF), fibroblast growth factor (FGF), platelet-derived growth factor (PDGF), insulin-like growth factor (IGF-I and II), TGF-□, vascular endothelial growth factor (VEGF) and the like. Other biologically active ligands include SMAD3, AXIN2, ID2, HEME Oxygenase-1 and Nell-1. Antibodies, including monoclonal antibodies, may also be covalently bound to the polymer surface.

When desired, an active agent (or a combination of active agents) can be bound to the polymer surface of a substrate by the organometallic layer according to the invention in order to accomplish any of a variety of goals. The particular active agent(s) used, as well as the mechanism to chemically and/or physically attach the active agent(s) to the derivatized surface, will obviously depend upon the chemical and/or physical nature of the derivatization of the surface, e.g., its reactivity, its functionality, its surface roughness, etc. Nevertheless, the following list of active agents that are suitable for surface immobilization according to the invention is merely exemplary and should not be construed as being complete.

In one embodiment, the active agent can include antileukotrienes or leukotriene receptor antagonists (e.g., for B4, C4, D4, and/or E4 leukotriene receptors) including, but not limited to, zafirlukast, montelukast, pranlukast, iralukast, pobilukast, or the like, or sombinations thereof, and/or salts thereof (e.g., Montelukast sodium, which is commercially available under the tradename SINGULAIR®).

In another embodiment, the active agent can include antihistamines including, but not limited to, ethanolamines (e.g., diphenhydramine and/or salts including hydro-chloride, dimenhydrinate, carbinoxamine, clemastine and/or salts such as fumarate, bromodiphenhydramine and/or salts such as hydrochloride, phenyloloxamine, doxyl-amine, or the like, or other salts thereof, or combinations thereof), ethylenediamines (e.g., tripelennamine and/or salts such as hydrochloride, pyrilamine and/or salts such as maleate, antazoline and/or salts such as phosphate, methapyriline, or the like, or other salts thereof, or combinations thereof), alkylamines (e.g., chlorpheniramine and/or salts such as maleate, brompheniramine and/or salts such as maleate, dexchlorpheniramine and/or salts such as maleate, dimethindene and/or salts such as maleate, triprolidine and/or salts such as hydrochloride, pheniramine and/or salts such as maleate, or the like, or other salts thereof, or combinations thereof), piper-zines (e.g., cyclizine and/or salts such as hydrochloride and/or lactate, meclizine and/or salts such as hydrochloride, hydroxyzine and/or salts such as hydrochloride and/or pamoate, buclizine, chlorcyclizine, or the like, or other salts thereof, or combinations thereof), phenothiazines (e.g., promethazine and/or salts such as hydrochloride, propiomazine, methdilazine, trimeprazine and/or salts such as tartrate, or the like, or other salts thereof, or combinations thereof), and/or miscellaneous others (e.g., cyproheptadine, ketotifen, azatadine and/or salts such as maleate, terfenadine, fexofenadine, astemizole, diphenylpyraline, phenindamine, or the like, or salts thereof, or combinations thereof).

In another embodiment, the active agent can include antiseptics including, but not 10 limited to, iodine, chlorhexidine acetate, sodium hypochlorite, and calcium hydroxide.

In another embodiment, the active agent can include steroidal anti-inflammatory agents including, but not limited to, betamethasone, triamcinolone, dexamethasone, prednisone, mometasone, fluticasone, beclomethasone, flunisolide, budesonide, or the like, or salts thereof, or combinations thereof. In another embodiment, the active agent can include non-steroidal anti-inflammatory agents including, but not limited to, fenoprofen, flurbiprofen, ibuprofen, ketoprofen, naproxen, oxaprozin, diclofenac, etodolac, indomethacin, ketorolac, nabumetone, sulindac, tolmetin, meclofenamate, mefenamic acid, piroxicam, suprofen, or the like, or salts thereof, or combinations thereof.

In another embodiment, the active agent can include decongestants including, but not limited to, ephedrine, phenylpropanolamine, pseudoephedrine, phenylephrine, epinephrine, ephedrine, desoxyephedrine, naphazoline, oxymetazoline, tetrahydro-zoline, xylometa7oline, propylhexedrine, or the like, or salts thereof, or combinations thereof.

In another embodiment, the active agent can include mucolytics including, but not limited to, acetylcysteine, dornase alpha, or the like, or salts thereof, or combinations thereof.

In another embodiment, the active agent can include anticholinergics including, but not limited to, ipratropium, atropine, scopolamine, or the like, or salts thereof, or combinations thereof.

In another embodiment, the active agent can include non-antibiotic antimicrobials including, but not limited to, taurolidine or the like.

In another embodiment, the active agent can include mast cell stabilizers including, but not limited to, cromolyn, nedocromil, ketotifen, salts thereof (e.g., sodium), or 10 combinations thereof.

In another embodiment, the active agent can include one or more active ingredients such as anti-infective agents, anti-inflammatory agents, mucolytic agents, antihistamines, antileukotrienes, decongestants, anticholinergics, antifungals, and combinations of these classes of agents. Anti-infective agents contemplated by the present invention include, but are not limited to antibiotics, anti-virals, non-antibiotic antimicrobials, and antiseptics. Anti-inflammatory agents contemplated by the present invention include, but are not limited to steroidal and non-steroidal anti-inflammatory agents, and mast cell inhibitors. Antifungal agents contemplated by the present invention include, but are not limited to amphotericin B, and azole antifungals. Examples of contemplated antibiotics include, but are not limited to cefuroxime, ciprofloxacin, tobramycin, cefoperazone, erythromycin, and gentamycin.

Exemplary anti-infective agents include, but are not limited to, penicillins, cephalo sporins, macrolides, ketolides, sulfonamides, quinolones, aminoglycosides, beta lactam antibiotics, and linezolid. Exemplary non-antibiotic antimicrobials include taurolidine. Exemplary steroidal anti-inflammatory agents include glucocorticoids. Exemplary non-steroidal anti-inflammatory agents include diclofenac. Exemplary mast cell stabilizers include cromolyn and nedcromil sodium. Exemplary mucolytic agents are acetylcysteine and dornase alpha. Exemplary decongestants are phenylephrine, naphazoline, oxymetazoline, tetrahydrozoline and xylometoazoline. Exemplary antihistamines include loratidine. Exemplary antibiotic combinations include cefuroxime and gentamicin Exemplary anticholinergics include ipratropium, atropine and scopolamine. Exemplary antifungals include amphotericin B, itraconazole, fluconazole, and miconazole.

In another embodiment, the active agent can include, but are not limited to, anti-inflammatory agents (e.g., alclometasone, amcinonide, amlexanox, balsalazide, betamethasone, celecoxib, choline magnesium, trisalicylate, choline salicylate, chlobetasol, colchicine, cortisone acetate, curcumin, disunite, dexamethasone, diclofenac, diflunisal, etodolac, fenoprofen, fluocinolone, fluometholone, flurandren-olide, flurandrenolide, flurbiprofen, hydrocortisone, ibuprofen, indomethacin, ketoprofen, ketorolac, meclofenamate, mefenamic acid, meloxicam, mesalamine, Methylprednisolone, nabumetone, naproxen, olsalazine, oxaprozin, piroxicam, prednisone, rofecoxib, salsalate, sulfasalazine, sulindac, tolmetin, triamcinolone, valdecoxiband, analogs/derivatives thereof, salts thereof, or combinations thereof), immunosuppressants (e.g., azathioprine, basiliximab, cyclosporine, daclizumab, leflunomide, lymphocyte immune globulin, methotrexate, muromonab-CD3, myco-phenolate, sirolimus, tacrolimus, thalidomideand, analogs/derivatives thereof, salts thereof, or combinations thereof), anti-cell proliferation agents (e.g., alkylating agents such as busulfan, cisplatin, cyclophosphamide, oxaliplatin, or the like; nitrosourea compounds such as in carmustine, lomustine, or the like; anthracycline compounds such as epirubicin, mitoxantrone, or the like; anti-androgen compounds such as bicalutamide, flutamide, nilutamide, or the like; antibiotics such as bleomycin, dactinomycin, mitomycin, or the like; anti-metabolite compounds such as cladribine, fluorouracil, gemcitabine, hydroxyurea, methotrexate, or the like; anti-microtubular compounds such as docetaxel, paclitaxel, or the like; aromatase inactivators such as anastrozole, exemestane, or the like; hormones such as estramumustine, megestrol, or the like; monoclonal antibody compounds such as alemtuzumab, rituximab, or the like; protein synthesis inhibitors such as asparaginase, pegaspargase, or the like; other compounds such as carboplatin, dipyridamole, doxorubin, doxorubicin, etopo-side, imatinib, misonidazole, mercaptopurine, testolactone, trimetrexate, glucuronate, tiripazamine, topotecan, vindesine, vincristine, analogs/derivatives thereof, salts thereof, or combinations thereof), anti-thrombosis, anti-platelet, and/or fibrinolysis agents (e.g., abcimab, antithrombin III, argatroban, aspirin, clopidogrel, dipyridamole, eptifibatide, fondaparinux, heparin, low molecular weight heparin, heparin sulfate, recombinant hirudin such as bivalirudin, lepirudin, or the like, ticlopidine, tissue recombinant plasminogen activators such as alteplase, reteplase, streptokinase, tenecteplase, urokinase, or the like, tirofibanand, analogs/derivatives thereof, salts thereof, or combinations thereof), extracellular matrix mediators (e.g., calprotectin, catechins, sulfonylated amino acid hydroxamates, tetracycline compounds such as demeclo-cycline, doxycycline, minocycline, oxytetracycline, tetracycline, or the like, analogs or derivatives thereof, salts thereof, or combinations thereof), and the like, and combinations thereof.

In another embodiment, the active agent can include, but are not limited to, anti-thrombotic agents such as heparin, heparin derivatives, urokinase, PPack (dextro-phenylalanine proline arginine chloromethylketone), or the like, analogs/derivatives thereof, salts thereof, or combinations thereof; steroidal and non-steroidal anti-inflammatory agents (NSAIDs) such as dexamethasone, prednisolone, cortico-sterone, hydrocortisone and budesonide estrogen, sulfasalazine and mesalamine, salicylic acid, salicylates, ibuprofen, naproxen, sulindac, diclofenac, piroxicam, ketoprofen, diflunisal, nabumetone, etodolac, oxaprozin, indomethacin, or the like, analogs/derivatives thereof, salts thereof, or combinations thereof; anti-neoplastic or anti-proliferative or antimitotic agents such as paclitaxel, 5-fluorouracil, cisplatin, vinblastine, vincristine, epothilones, endostatin, angiostatin, doxorubicin, metho-trexate, angiopeptin or the like, analogs/derivatives thereof, salts thereof, or combinations thereof; monoclonal antibodies capable of blocking smooth muscle cell proliferation, thymidine kinase inhibitors, or the like, analogs/derivatives thereof, salts thereof, or combinations thereof; anesthetic agents such as lidocaine, bupivacaine, ropivacaine, or the like, analogs/derivatives thereof, salts thereof, or combinations thereof; anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors, tick antiplatelet peptides, or the like, analogs/derivatives thereof, salts thereof, or combinations thereof; vascular cell growth promoters such as growth factors, transcriptional activators, translational promoters, or the like, analogs/derivatives thereof, salts thereof, or combinations thereof; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, or the like, analogs/derivatives thereof, salts thereof, or combinations thereof; protein kinase and tyrosine kinase inhibitors such as tyrphostins, genistein, quinoxalines, or the like, analogs/derivatives thereof, salts thereof, or combinations thereof; prostacyclin analogs; cholesterol-lowering agents; angiopoietins; resveratrol and derivatives thereof; antimicrobial agents such as triclosan, cephalosporins, 13-lactams, aminoglycosides, nitrofurantoin, or the like, analogs/derivatives thereof, salts thereof, or combinations thereof; cytotoxic agents; cytostatic agents; cell proliferation affectors; vasodilating agents; agents that interfere with endogenous vasoactive mechanisms; analogs/derivatives thereof; salts thereof; metabolites thereof; or combinations thereof.

Exemplary genetic active agents include, but are not limited to, anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Such molecules include any of the "hedgehog" proteins, or the DNA's encoding them.

Vectors of interest for delivery of genetic active agents include, but are not limited to, (a) plasmids, (b) viral vectors such as adenovirus, adeno-associated virus, lentivirus, or the like, and (c) non-viral vectors such as lipids, liposomes, cationic lipids, or the like. Cells include cells of human origin (autologous or allogenic), including stem cells, or from an animal source (xenogenic), which can be genetically engineered if desired to deliver proteins of interest.

Non-limiting examples of useful antimicrobial agents include: Antiamebics, e.g., Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Diphetarsone, Emetine, Fumagillin, Glaucarubin, Glycobiarsol, 8-Hydroxy-7-iodo-5-quinoline-sulfonic Acid, Iodochlorhydroxyquin, Iodoquinol, Paromomycin, Phanquinone, Polybenzarsol, Propamidine, Quinfamide, Scenida7ole, Sulfarside, Teclozan, Tetracycline, Thiocarbamizine, Thiocarbarsone, Timidazole; Antibiotics, e.g. Amino-glycosides (such as Amikacin, Apramycin, Arbekacin, Bambermycins, Butirosin, Dibekacin, Dihydrostreptomycin, Fortimicin(s), Gentamicin, Isepamicin, Kaniamycin, Micronomicin, Neomycin, Neomycin Undecylenate, Netilmicin, Paromomycin, Ribostamycin, Sisomicin, Spectinomycin, Streptomycin, Tobramycin, Trospectomycin, and the like), Amphenicols (such as Azidamfenicol, Chloramphenicol, Florfenicol, Thiamphenicol, and the like), Ansamycins (such as Rifamide, Rifampin, Rifamycin, Rifapentine, Rifaximin, and the like), 13-Lactams (e.g., Carbacephems, Loracarbef, Carbapenems (such as Biapenem, Imipenem, Meropenem, Panipenem, and the like), Cephalosporins (such as Cefaclor, Cefadroxil, Cefamandole, Cefatrizine, Cefazedone, Cefazolin, Cefcapene Povoxil, Cefclidin, Cefdinir, Cefditoren, Cefepime, Cefetamet, Cefixime, Cefinenoxine, Cefodizime, Cefonicid, Cefoperazone, Ceforanide, Cefotaxime, Cefotiam, Cefozopran, Cefpimizole, Cefpiramide, Cefpirome, Cefpodoxime Proxetil, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin, and the like), Cepha-mycins (such as Cefbuperazone, Cefinetazole, Cefminox, Cefotetan, Cefoxitin, and the like), Monobactams (such as Aztreonam, Carumonam, Tigemonam, and the like), Oxacephens (such as Flomoxef, Moxalactam, and the like), Penicillins (such as Amdinocillin, Amdinocillin Pivoxil, Amoxicillin, Ampicillin, Apalcillin, Aspoxicillin, Azidocillin, Azlocillin, Bacampicillin, Benzylpenicillic Acid, Benzylpenicillin Sodium, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Mezlocillin, Naacillin Sodium, Oxacillin, Penamecillin, Penethamate Hydro-iodide, Penicillin G Benethamine, Penicillin G Benzathine, Penicillin G Benzhydryl-amine, Penicillin G Calcium, Penicillin G Hydrabamine, Penicillin G Potassium, Penicillin G Procaine, Penicillin N, Penicillin 0, Penicillin V, Penicllin V Benzathine, Penicillin V Hydrabamine, Penimepicycline, Phenethicillin Potassium, Pipera-cillin, Pivampicillin, Propicillin, Quinacillin, Sulbenicillin, Sultamicillin, Talampicillin, Temocillin, Ticarcillin, and the like), Ritipenem, Lincosamides (such as Clindamycin, Linco-mycin, and the like), Macrolides (such as Azithromycin, Capbomycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin, Troleandomycin, and the like), poly-peptides (such as Amphomycin, Bacitracin, Capreomycin, Colistin, Enduracidin, Envio-mycin, Fusafungine, Gramicidin S, Gramicidin(s), Mikamycin, Polymyxin, Pristinamycin, Ristocetin, Teicoplanin, Thiostrepton, Tuberactinomycin, Tyrocidine, Tyrothricin, Vancomycin, Viomycin, Virginiamycin, Zinc Bacitracin, and the like), Tetracyclines (such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Tetracycline, and the like), Cycloserine, Mupirocin, Tuberin; synthetic antibacterial agents, e.g. 2,4-Diaminopyrimi-dines (such as Brodimoprim, Textroxoprim, Trimethoprim, and the like), Nitrofurans (such as Furaltadone, Furazolium Chloride, Nifuradene, Nifuratel, Nifurfoline, Nifur-pirinol, Nifurprazine, Nifurtoinol, Nitrofurantoin, and the like), Quinolones and Analogs (such as Cinoxacin, Ciprofloxacin, Clinafloxacin, Difloxacin, Enoxacin, Fleroxacin, Flumequine, Grepafloxacin, Lomefloxacin, Miloxacin, Nadifloxacin, Nadilixic Acid, Norflaxacin, Ofloxacin, Oxolinic Acid, Pazufloxacin, Pefloxacin, Pipemidic Acid, Piromidic Acid, Rosoxacin, Rufloxacin, Sparfloxacin, Temafloxacin, Tosufloxacin, Trovafloxacin, and the like), Sulfonamides (such as Acetyl Sulfamethoxpyrazine, Benzylsulfamide, Chloramine-B, Chloramine-T, Dichloramine T, N2-Formylsulfisomidine, N4-y-D-Glucosylsulfanilamide, Mafenide, 4'-(Methylsulfamoyl)sulfanil-anilide, Noprylsulfamide, Phthalylsulfacetamide, Phthalylsulfathiazole, Salazo-sulfadimidine, Succinylsulfathiazole, Sulfabenzamide, Sulfacetamide, Sulfachlor-pyrida7ine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic, Sulfamerazine, Sulfameter, Sulfamethazine, Sulfamethizole, Sulfa-methomidine, Sulfamethoxazole, Sulfamethoxypyridazine, Sulfametrole, Sulfamido-chrysoidine, Sulfamoxole, Sulfanilamide, 4-Sulfanilamidosalicylic Acid, N4-Sulfanilyl-sulfanilamide, Sulfanilylurea, N-Sulfanilyl-3,4-xylamide, Sulfanitran, Sulfaperine, Sulfaphenazole, Sulfaproxyline, Sulfapyrazine, Sulfapyri-dine, Sulfasomizole, Sulfa-symazine, Sulfathiazole, Sulfathiourea; Sulfatolamide, Sulfisomi-dine, Sulfisoxazole, and the like), Sulfones (such as Acedapsone, Acediasulfone, Acetosul-fone Sodium, Dapsone, Diathymosulfone, Glucosulfone Sodium, Solasulfone, Succisulfone, Sulf-anilic Acid, p-Sulfanilylbenzylamine, Sulfoxone Sodium, Thiazolsulfone, and the like), Clofoctol, Hexedine, Methenamine, Methenamine Anhydromethylenecitrate, Methenamine Hippurate, Methenamine Mandelate, Methenamine Sulfosalicylate, Nitroxoline, Taurolidine, Xibomol, and the like; leprostatic antibacterial agents, such as Acedapsone, Acetosulfone Sodium, Clofazimine, Dapsone, Diathymosulfone, Glucosulfone Sodium, Hydnocarpic Acid, Solasulfone, Succisulfone, Sulfoxone Sodium, and the like, antifungal agents such as Allyl-amines Butenafine, Naftifine, Terbinafine, Imidazoles (e.g., Bifonazole, Butoconazole, Cholordantoin, Chlormid-azole, Cloconazole, Clotrimazole, Econazole, Enilconazole, Fenticonazole, Flutrimazole, Isoconazole, Ketoconazole, Lanoconazole, Miconazole, Omoconazole, Oxiconazole Nitrate, Sertaconazole, Sulconazole, Tioconazole, and the like), Thiocarbamates (e.g., Tolcilate, Tolindate, Tolnaftate, and the like), Triazoles (e.g., Fluconazole, Itraconazole, Saperconazole, Terconazole, and the like), Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, Zinc Propionate, etc.; or the like; analogs/derivatives thereof; salts thereof; or combinations thereof.

Other antimicrobial agents useful in the present invention include, but are not limited to, Q-lactamase inhibitors (e.g. Clavulanic Acid, Sulbactam, Tazobactam, and the like); Chloramphenicols (e.g. Azidamphenicol, Chloramphenicol, Thiaphenicol, and the like); Fusidic Acid; synthetic agents such as Trimethoprim, (optionally in combin-ation with sulfonamides) Nitroimidazoles (e.g., Metronidazole, Tinidazole, Nimor-azole, and the like), and the like; Antimycobacterial agents (e.g., Capreomycin, Clofazimine, Dapsone, Ethambutol, Isoniazid, Pyrazinamide, Rifabutin, Rifampicin, Streptomycin, Thioamides, and the like); Antiviral agents (e.g., Acryclovir, Amanta-dine, Azidothymidine, Ganciclovir, Idoxuridine, Tribavirin, Trifluridine, Vidarabine, and the like); Interferons; antiseptic agents (e.g., Chlorhexidine, Gentian violet, Octenidine, Povidone Iodine, Quaternary ammonium compounds, Silver sulfadi-azine, Triclosan, and the like); or the like; analogs/derivatives thereof; salts thereof; or combinations thereof.

In some embodiments, the active agent may include, but is not limited to, collagen (e.g., Type 1), osteonectin, bone sialoproteins (Bsp), alpha-2HS-glycoproteins, bone Glaprotein (Bgp), matrix Gla-protein, bone phosphoglycoprotein, bone phosphor-protein, bone proteoglycan, protolipids, bone morphogenic proteins (e.g., BMP-1, -2A, -2B, -3, -3b, -4, -5, -6, -7, -8, -8b, -9, -10, -11, -12, -13, -14, -15), cartilage induction factor, platelet derived growth factor (PDGF-1, -2), endothelial cell growth factors (ECGF-1, -2a, -2b), skeletal growth factor (SKF=IGF-2), insulin-like growth factors (IGF-1, IGF-2), fibroblast growth factor (ODGF-1, -2, -3, -4, -5, -6, -7, -8, -9, -10, -11, -12, -13, -14, -15, -16, -17, -18, -19, -20, -21, -22, -23), colony stimulating factor, transforming growth factor (e.g., TGF-a, TGF-(3, or the like), vascular endothelial growth factors (VEGF), growth/differentiation factors (GDF-1, -3, -5, -6, -7, -8, -9, -9B, -10, -11, -15, -16), osteogenic proteins (OP-1=BMP-7, OP-2=BMP-8, OP-3=BMP-8b), bone growth hormone, parathyroid hormone (PTH), insulin, calcitonin, and the like, and combinations thereof. Additionally or alternately, the active agents may include proteins associated with cartilage, such as chondrocalcining protein; proteins associated with dentin, such as phosphophoryn, glycoproteins and Gla proteins; proteins associated with enamel such as amelognin and enamelin; structural proteins such as fibrin, fibrinogen, keratin, tubulin, elastin, and the like; blood proteins, whether in plasma or serum, e.g., serum albumin; non-protein growth factors such as prostaglandins and statins (e.g., Simvastatin, Lovastatin, or the like); or the like; analogs/derivatives thereof; salts thereof; or combinations thereof.

In another embodiment, the active agent can include amino acids, anabolics, analgesics and antagonists, anesthetics, angiogenesis agents, anti-angiogenetic agents, antihelmintics, anti-adrenergic agents, anti-asthmatics, anti-atherosclerotics, antibacterials, anticholesterolics, anticholinergics, anti-coagulants, antidepressants, antidotes, anti-emetics, anti-epileptic drugs, anti-fibrinolytics, antihistamines, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media and radioisotopes), drugs for treatment of chronic alcoholism, drugs targeting dopaminergic pathways, electrolytes, enzymes, enzyme inhibitors, ferments, ferment inhibitors, gangliosides and ganglioside derivatives, hemostatics, hormones, hormone antagonists, hypnotics, immuno-modulators, immunostimulants, immuno-suppressants, minerals, muscle relaxants, neuron-modulators, neurotransmitters and neurotropics, osmotic diuretics, parasympatholytics, parasympathomimetics, peptides, proteins, psychostimulants, respiratory stimulants, sedatives, serum lipid reducing agents, smooth muscle relaxants, sympatholytics, sympathomimetics, vasodilators, vaso-protectives, vectors for gene therapy, viral vaccines, viruses, vitamins, oligonucleotides and derivatives, or the like, or analogs/derivatives thereof, salts thereof, and/or combinations thereof.

In another embodiment, the active agent can include antimicrobial agents, analgesics, antiinflammatory agents, counter irritants coagulation modifying agents, diuretics, sympatho-mimetics, anorexics, antacids and other gastrointestinal agents, antiparasitics, antidepressants, antihypertensives, anticholinergics, stimulants, antihormones, central and respiratory stimu-lants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvul-sants, antihist-amines, beta-blockers, purgatives, antiarrhytmics, contrast materials, radio-pharmaceuticals, antiallergic agents, tranquilizers, vasodilators, antiviral agents, and anti-neoplastic or cytostatic agents or other agents with anticancer properties, vitamins (including micro- and macro-nutrients), or a combination thereof.

In another embodiment, the active agent includes an anti-muscle spasm agent, anti-spasmodic, bone resorption inhibitor, smooth muscle contractile agent, calcium absorption enhancer, muscle relaxant, or a mixture thereof. Suitable anti-muscle spasm agents include, but are not limited to, baclofen, botulinum toxin, carisoprodol, chlorphenesin, chlorzoxazone, cyclobenzaprine, dantrolene, diazepam, metaxalone, methocarbamol, orphenadrine, tizani-dine, and mixtures thereof. Suitable anti-spasmodics include, but are not limited to, atropine, baclofen, dicyclomine, hyoscine, propatheline, oxybutynin, S-oxybutynin, tizanidine, cevimeline, chlordiazepoxide, hydrochloride, dicyclomine, hyoscine, hyoscyamine, glycopyrrolate, and mixtures thereof. Suitable bone resorption inhibitors include, but are not limited to alendronate, ibandronate, minodronate, risedronate, etidronate, tiludronate, and mixtures thereof. A suitable smooth muscle contractile agent includes, but is not limited to, hyoscine, and mixtures thereof. Suitable calcium absorption enhancers include, but are not limited to, alfacalcidol, calcitriol, and mixtures thereof. Suitable muscle relaxants include, but are not limited to, baclofen, carisoprodol, chlorphenesin, chlorzoxazone, cyclobenzaprine, dantrolene, diazepam, metaxalone, methocarbamol, orphenadrine, and mixtures thereof.

In another embodiment, the active agent includes an anti-diuretic, anti-muscle spasm agent, anti-spasmodic, agent for treating urinary incontinence, anti-diarrheal agent, agent for treating nausea and/or vomiting, smooth muscle contractile agent, anti-secretory agent, enzyme, anti-ulcerant, bile acid replacement and/or gallstone solubilizing drug, or a mixture thereof. Suitable anti-diuretics include, but are not limited to, acetazolamide, benzthiazide, bendroflumethazide, bumetanide, chlorthali-done, chlorothiazide, ethacrynic acid, furosemide, hydrochlorothiazide, hydroflume-thiazide, methyclothiazide, polythiazide, quinethazone, spironolactone, triamterene, torsemide, trichlomethiazide, desmopressin, oxytocin, and mixtures thereof. Suitable anti-muscle spasm agents include, but are not limited to, baclofen, botulinum toxin, carisoprodol, chlorphenesin, chlorzoxazone, cyclobenzaprine, dantrolene, diazepam, metaxalone, methocarbamol, orphenadrine, tizanidine, and mixtures thereof. Suitable anti-spasmodics include, but are not limited to, atropine, baclofen, dicyclomine, hyoscine, propatheline, oxybutynin, S-oxybutynin, tizanidine, and mixtures thereof. Suitable agents for treating urinary incontinence include, but are not limited to, darifenacin, vamic-amide, detrol, ditropan, imipramine, and mixtures thereof. Suitable anti-diarrheal agents include, but are not limited to, ondansetron, palnosetron, tropisetron, attapulgite, atropine, bismuth, diphenoxylate, loperamide, and mixtures thereof. Suitable agents for treating nausea and/or vomiting include, but are not limited to, alosetron, dolasetron, granisetron, meclizine, metoclopramide, ondansetron, palnosetron, prochloperazine, promethazine, trimethobenzamiode, tropisetron, and mixtures thereof. A suitable smooth muscle contractile agent includes, but is not limited to, hyoscine. Suitable anti-secretory agents include, but are not limited to, esomeprazole, lansoprazole, omeprazole, pantoprazole, rabeprazole, tenetopra-zole, ecabet, misoprostol, teprenone, and mixtures thereof. Suitable enzymes include, but are not limited to, alpha-galactosidase, alpha-L-iduronidase, imiglucerase/alglucerase, amylase, lipase, protease, pancreatin, olsalazine, and mixtures thereof. Suitable anti-ulcerants include, but are not limited to, cimetidine, ranitidine, famotidine, misoprostol, sucralfate, pantopra-zole, lansoprazole, omepra-zole, and mixtures thereof. A suitable bile acid replacement and/or gallstone solubilizing drug includes, but is not limited to, ursodiol.

In another embodiment, the active agent includes an endocrine modulator, glucose production inhibitor, agent for treatment of type II diabetes, anti-secretory agent, glycolipid, glycoprotein, anti-hyperthyroid agent, thyroid hormone, or a mixture thereof. Suitable endocrine modulators include, but are not limited to, methimazole, voglibose, finasteride, GI198745, liothyronine, glyburide, metformin, nateglinide, ioglitazone, pegvisomant, minoxidil, and mixtures thereof. Suitable glucose production inhibitors include, but are not limited to, acarbose, acetohexamide, chlorpropamide, glipizide, glyburide, metformin, miglitol, nateglinide, pioglitAzone, rosiglitazone, tolbutamide, tolazamide, and mixtures thereof. Suitable agents for treatment of type II diabetes include, but are not limited to, acarbose, acetohex-amide, chlorpropamide, glipizide, glyburide, metformin, miglitol, nateglinide, pioglit-azone, rosiglitazone, tolbutamide, tolazamide, and mixtures thereof. Suitable anti-secretory agents include, but are not limited to, esomeprazole, lansoprazole, omeprazole, pantoprazole, rabeprazole, tenetoprazole, ecabet, misoprostol, teprenone, and mixtures thereof. Suitable glycolipids include, but are not limited to imigulcerase, vancomycin, vevesca (OGT 918), GMK vaccine, and mixtures thereof. Suitable glycoproteins include, but are not limited to, staphvax, bimosiamose (TBC1269), GCS-100, heparin, and mixtures thereof. Suitable anti-hyperthyroid agents include, but are not limited to, methimazol, propylthiouracil, and mixtures thereof.

In another embodiment, the active agent includes a cholesterol-lowering agent, aldosterone antagonist, triglyceride-lowering agent, leukotriene receptor antagonist, immunomodulator or immunogen, glucose production inhibitor, agent for treatment of type II diabetes, bone resorption inhibitor, calcium absorption enhancer, insulin enhancing agent, insulin sensitizer, cytokine, metabolic regulator, mast cell mediator, eosinophil and/or mast cell antagonist, glycolipid, glycoprotein, anti-inflammatory drug, anti-obesity drug, COX (cyclooxygenase) and/or LO (lipoxygenase) inhibitor, or a mixture thereof. Suitable cholesterol-lowering agents include, but are not limited to, atorvastatin, benzofibrate, bezafibrate, cerivastatin, cholestyramine, ciprofibrate, clofibrate, colesevelam, colestipol, ezetimibe, fluvastatin, gemfibrozil, lovastatin, niacin/lovastatin, pravastatin, probucol, rosuvastatin, and simvastatin. A suitable aldosterone antagonist includes, but is not limited to, spironolactone. A suitable triglyceride-lowering agent includes, but is not limited to, fenofibrate. Suitable immunomodulators or immunogens include, but are not limited to, interferon beta 1A, interferon beta 1B. Suitable glucose production inhibitors include, but are not limited to, acarbose, acetohexamide, chlorpropamide, glipizide, glyburide, metformin, miglitol, nateglinide, pioglitazone, rosiglitazone, tolbutamide, and tolazamide. Suitable insulin enhancing agents include, but are not limited to, acamprosate, miglitol, troglitazone, chlorpropamide, glimepiride, glipizide, glyburide, and repaglinide. A suitable insulin sensitizer includes, but is not limited to, is BRL 49653. Suitable cytokines include, but are not limited to, darbepoetin alfa, epoetin alpha, erythropoietin, and NESP. Suitable metabolic regulators include, but are not limited to, allopurinol and oxypurinol. A suitable eosinophil and/or mast cell antagonists includes, but is not limited to, nedocromil. Suitable anti-inflammatory drugs include, but are not limited to, alosetron, anakinra, beclomethasone, betamethasone, budesonide, clobetasol, celecoxib, cromolyn, desoximetasone, dexamethasone, epinastic, etanercept, etoricoxib, flunisolide, fluocinonide, fluticasone, formoterol, hydrocortisone, hydroxychloroquine, ibudilast, ketotifen, meloxicam, mesalamine, methotrexate, methylprednisolone, mometasone, montelukast, nedocromil, olsalazine, prednisone, ramatroban, rofecoxib, salsalate, terbutaline, triamcinolone, valdecoxib, and zafirlukast. Suitable anti-obesity drugs include, but are not limited to, dexedrine, diethylpropion, mazindol, oleoyl-estrone, phentermine, phendimetrazine, and sibutramine. A suitable COX and/or LO inhibitor includes, but is not limited to, is ML-3000.

In another embodiment, the active agent includes an anti-arrhythmic, anti-hypertensive, heart regulator, cardiovascular agent, plaque stabilization agent, vasodilator, antianginal, anti-coagulant, anti-hypotensive, anti-thrombotic, drug for treating congestive heart failure, p-FOX (fatty acid oxidation) inhibitor, or a mixture thereof. Suitable antiarrhythmics include, but are not limited to, adenosine, amioda-rone, bepridil, bretylium, digitoxin, digoxin, diltiazem, disopyramide, dofetilide, D-sotolol, flecamide, lidocaine, mexiletine, milrinone, phenyloin, pilsicamide, procain-amide, propafenone, propranolol, quinidine, tocamide, dofetilide, and mixtures thereof. Suitable anti-hypertensives include, but are not limited to, acebutolol, alfuzosin, amlodipine, atenolol, amlodipine/benazepril, barnidipine benazepril, bepridil, betaxolol, bisoprolol, bosentan, candesartan, captopril, cariporide, carvedilol, celiprolol, cilazapril, clonidine, diltiazem, doxazosin, enalapril, eplerenone, eprosartan, esmolol, felodipine, fenoldopam, fosinopril, guanfacine, imidapril, irbesartan, isradipine, labetalol, lercanidipine, lisinopril, losartan, manidipine, methyldopa, metoprolol, moxonidine, nadolol, nicardipine, nicorandal, nifedipine, nitrendipine, nosoldipine, omapatrilat, perindopril erbumine, pindolol, prazosin, propranolol, quinapril, ramipri, sotalol, spirapril, tamsulosin, telmisartan, terazosin, torsemide, trandolapril, valsartan, vatanidipine, midodrine, and mixtures thereof. Suitable heart regulators include, but are not limited to, digoxin, digitoxin, dobut-amine, and mixtures thereof. Suitable cardiovascular agents include, but are not limited to, edaravone, iloprost, levosimendan, molsidomine, tezosentan, tirilazad, YM087, adenosine, avasimibe, fenofibrate, and mixtures thereof. A suitable plaque stabilization agent includes, but is not limited to, avasimibe. Suitable vasodilators include, but are not limited to, buflomedil, cilostazol, dipyridamole, diazoxide, hydralazine, minoxidil, naftidrofuryl, nicorandil, nitroprusside, alprostadil, apomorphine, phentolamine mesylate, sildenafil, tadalafil, vardenifil, and mixtures thereof. Suitable anti-anginals include, but are not limited to, amilodipine, amyl nitrite, atenolol, bepridil, diltiazem, erythrityl tetranitrate, felodipine, isosorbide dinitrate, isradipine, metoprolol, nadolol, nicardipine, nifedipine, nimodipine, pentaerythritol tetranitrate, propranolol, and mixtures thereof. Suitable anti-coagulants include, but are not limited to, abciximab, ardeparin, argatroban, bivalirudin, clopidogrel, dalteparin, danaparoid, desirudin, dipyridamole, enoxaparin, eptifibatide, fondaparinux, H376/95, lepirudin, melagatran, nadroparine, nafamostat mesilate, pentosan, pentoxifylline, reviparin, sarpogrelate, SNAC/SNAD-heparin, ticlopidine, tinzaparin, tirofiban, warfarin, and mixtures thereof. Suitable anti-hypotensives include, but are not limited to, midodrine, dobutamine, fludrocortisone, and mixtures thereof. Suitable anti-thrombotics include, but are not limited to, aspirin, abciximab, enoxaparin, integrelin, ticlopidine, and mixtures thereof. Suitable drugs for treating congestive heart failure include, but are not limited to, aminone, benazepril, bumetanide, captopril, digitoxin, digoxin, dobutamine, dopamine, enalapril, ethacrynic acid, fosino-pril, furosemide, hydralazine, lisinopril, milrinone, minoxidil, moexipril, quinapril, ramipril, torsemide, and mixtures thereof. A suitable p FOX inhibitor includes, but is not limited to, ranolazine.

In another embodiment, the active agent includes an aldosterone antagonist, immunomodulator or immunogen, immunosuppressant, cytokine, leukotriene receptor antagonist, mast cell mediator, eosinophil and/or mast cell antagonist, mucolytic, glucocorticoid, glycolipid, or a mixture thereof. A suitable aldosterone antagonist includes, but is not limited to, spironolactone. Suitable immuno-suppressants include, but are not limited to, azathioprine, cyclophosphamide, cyclosporine, ERL 080, enlimomab, methotrexate, mitoxantrone, mycophenolate, mofetil, sirolimus, tacrolimus (FK-506), and mixtures thereof. Suitable mucolytics for use in the buccal sprays of the invention include, but are not limited to, ambroxol, bromhexin, fudostein, acetylcestine, and mixtures thereof.

In another embodiment, the active compound is a p-FOX (fatty acid oxidation) inhibitor, acetylcholinesterase inhibitor, nerve impulse inhibitor, anti-cholinergic, anti-convulsant, anti-psychotic, anxiolytic agent, dopamine metabolism inhibitor, agent to treat post stroke sequelae, neuroprotectant, agent to treat Alzheimer's disease, neurotransmitter, neurotransmitter agonist, sedative, agent for treating attention deficit disorder, agent for treating narcolepsy, central adregenic antagonist, anti-depression agent, agent for treating Parkinson's disease, benzodiazepine antagonist, stimulant, neurotransmitter antagonist, tranquilizer, or a mixture thereof. Suitable acetylcholinesterase inhibitors include, but are not limited to, galantamine, neostig-mine, physostigmine, and edrophonium. Suitable nerve impulse inhibitors include, but are not limited to, levobupivacaine, lidocaine, prilocalne, mepivacaine, propofol, rapacuronium bromide, ropivacaine, tubocurarine, atracurium, doxaurium, miva-curium, pancuronium, vercuronium, pipecuronium, and rocuronium. Suitable anti-cholinergics for use in the buccal sprays of the invention include, but are not limited to, amantadine, ipratropium, oxitropium, and dicycloverine. Suitable anti-convulsants include, but are not limited to, acetazolamide, carbamazepine, clonazepam, diazepam, divalproex (valproic acid), ethosuximide, lamotrignine acid, levetriacetam, oxcarbazepine, phenol-barbital, phenyloin, pregabalin, primidone, remacemide, trimethadione, topiramate, vigabatrin, and zonisamide. Suitable antipsychotics include, but are not limited to, amisulpride, aripiprazole bifemelane, bromperidol, clozapine, chlorpromazine, haloperidol, iloperidone loperidone, olanzapine, quetiapine, fluphenazine, fumarate, risperidone, thiothixene, thioridazine, sulpride, and ziprasidone. Suitable anxiolytic agents include, but are not limited to, amitryptiline, atracurium, buspirone, chlorzoxazone, clorazepate, cisatracurium, cyclobenzaprine, eperisone, esopiclone, hydroxyzine, mirtazapine, mivacurium, pagoclone, sulperide, zaleplon, and zopiclone. Suitable dopamine metabolism inhibitors include, but are not limited to, entacapone, lazebemide, selegiline, and tolcapone. Suitable agents to treat post stroke sequelae include, but are not limited to, glatiramer, interferon beta 1A, interferon beta 1B, estradiol, and progesterone. Suitable neuron-protectants include, but are not limited to, donepezil, memanine, nimodipine, riluzole, rivastigmine, tacrine, TAK147, and xaliproden. Suitable agents to treat Alzheimer's disease include, but are not limited to, carbidopa, levodopa, tacrine, donezepil, rivastigmine, and galantamine. Suitable neurotransmitters include, but are not limited to, acetylcholine, serotonin, 5-hydroxytryptamine (5-HT), GABA, glutamate, aspartate, glycine, histamine, epinephrine, norpinephrine, dopamine, adenosine, ATP, and nitric oxide. Suitable neuron-transmitter agonists include, but are not limited to, almotriptan, aniracetam, atomoxetine, benserazide, bromocriptine, bupropion, cabergoline, citalopram, clomipramine, desipramine, diazepam, dihydroergotamine, doxepin duloxetine, eletriptan, escitalopram, fluvoxamine, gabapentin, imipramine, moclobemide, naratriptan, nefazodone, nefiracetam acamprosate, nicergoline, nortryptiline, paroxetine, pergolide, pramipexole, rizatriptan, ropinirole, sertraline, sibutramine, sumatriptan, tiagabine, trazodone, venlafaxine, and zolmitriptan. Suitable sedatives include, but are not limited to, dexmedetomidine, eszopiclone, indiplon, zolpidem, and zaleplon. Suitable agents for treating attention deficit disorder include, but are not limited to, amphetamine, dextroamphetamine, methyl-phenidate, and pemoline. Suitable agents for treating narcolepsy include, but are not limited to, modafinil and mazindol. A suitable central adregenic antagonist includes, but is not limited to, mesoridazine Suitable anti-depression agents include, but are not limited to, amitriptyline, amoxapine, bupropion, clomipramine, clomipramine, clorgyline, desipramine, doxepin, fluoxetine, imipramine, isocarboxazid, maprotiline, mirtazapine, nefazodone, nortriptyline, paroxetine, phenelzine, protriptyline, sertraline, tranylcypromine, trazodone, and venlafaxine. Suitable agents for treating Parkinson's disease include, but are not limited to, amantadine, bromocriptine, carvidopa, levodopa, pergolide, and selegiline. A suitable benzo-diazepine antagonist includes, but is not limited to, flumazenil. A suitable neuron-transmitter antagonist includes, but is not limited, to deramciclane. Suitable stimulants include, but are not limited to, amphetamine, dextroamphetamine, dinoprostone, methylphenidate, methylphenidate, modafinil, and pemoline A suitable tranquilizer includes, but is not limited to, mesoridazine.

In another embodiment, the active agent includes a nerve impulse inhibitor. Suitable nerve impulse inhibitors include, but are not limited to levobupivacaine, lidocaine, prilocalne, mep-ivacaine, propofol, rapacuronium bromide, ropivacaine, tubocurarine, atracurium, doxacurium, mivacurium, pancuronium, vecuronium, pipecuronium, rocuronium, and mixtures thereof.

In another embodiment, the active agent includes an anti-opioid agent. Suitable anti-opioid agents for use in the buccal sprays of the invention include, but are not limited to, naloxone, nalmefene, naltrexone, cholecystokinin, nociceptin, neuropeptide FF, oxytocin, vasopressin, and mixtures thereof.

In another embodiment, the active agent includes an anti-migraine agent. Suitable anti-migraine agents for use in the buccal sprays of the invention include, but are not limited to, frovatriptan, zolmitriptan, rizatriptan, almotriptan, eletriptan, naratriptan, almotriptan, ergotamine, diethylergotamine, sumatriptan, and mixtures thereof.

In another embodiment, the active agent includes a pain control agent. Suitable pain control agents for use in the buccal sprays of the invention include, but are not limited to, non-steroidal anti-inflammatory drugs, alfentanil, butorphanol, codeine, dezocine, fentanyl, hydrocodone, hydromorphone, levorphanol, meperidine, methadone, morphine, nalbuphine, oxycodone, oxymorphone, propoxyphene, pentazocine, sufentanil, tramadol, and mixtures thereof.

In another embodiment, the active agent includes an anesthetic. Suitable anesthetics for use in the buccal sprays of the invention include, but are not limited to, benzo-natate, bupivacaine, desflurane, enflurane, isoflurane, levobupivacaine, lidocaine, mepivacaine, prilocalne, propofol, rapacuronium bromide, ropivacaine, sevoflurane, ketamine, and mixtures thereof.

In another embodiment, the active agent can include, but is not limited to, cyclo sporine, sermorelin, octreotide acetate, calcitonin-salmon, insulin lispro, sumatriptan succinate, clozepine, cyclobenzaprine, dexfenfluramine hydrochloride, glyburide, zidovudine, erythromycin, ciprofloxacin, ondansetron hydrochloride, dimenhydrinate, cimetidine hydro-chloride, famotidine, phenyloin sodium, phenyloin, carboprost thromethamine, carboprost, diphenhydramine hydrochloride, isoproterenol hydrochloride, terbutaline sulfate, terbutaline, theophylline, albuterol sulfate, neutraceuticals (i.e., nutrients with pharmacological action, e.g., carnitine, valerian, echinacea, and the like), or the like; analogs/derivatives thereof; salts/alternate salts thereof; or combinations thereof.

Any opioid or non-µ-opioid, a pharmaceutically acceptable salt thereof, a base form thereof, or mixture of any combination of such opioids and/or their derivatives that are known in the art can be included. Opioids believed to have at least some µ-opioid receptor agonist activity (and optionally at least some agonist activity also at one or more of the κ-opioid receptor, the δ-opioid receptor, and the ORL-1 receptor) include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydro-codeine, dihydromorphine, dihydromorphine, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, and mixtures thereof. Non-µ-opioids include, but are not limited to, ORL-1-specific opioid agonists, such as nociceptin, deltorphin, and the like, and mixtures thereof. In a preferred embodiment, the opioid includes buprenorphine, pharmaceutically acceptable salts thereof, base forms thereof, fentanyl, pharmaceutically acceptable salts thereof, base forms thereof, oxycodone, pharmaceutically acceptable salts thereof, base forms thereof, and any combination of such opioids and/or their derivatives.

In certain embodiments, the opioid agonist includes hydrocodone, morphine, hydromorphone, oxycodone, codeine, levorphanol, meperidine, methadone, oxymorphone, buprenorphine, fentanyl, dipipanone, heroin, tramadol, etorphine, dihydroetorphine, butorphanol, levorphanol, pharmaceutically acceptable salts thereof, base forms thereof, and any and all mixtures thereof. The opioid agonist can, in some embodiments, include oxycodone, hydrocodone, fentanyl, buprenorphine, pharmaceutically acceptable salts thereof, base forms thereof, and any and all mixtures thereof. The opioid agonist can, in other embodiments, include buprenorphine, pharmaceutically acceptable salts thereof, base forms thereof, fentanyl, pharmaceutically acceptable salts thereof, base forms thereof, and any combination of such opioids and/or their derivatives.

General categories of active agents can, in one embodiment, include, but are not limited to: ACE inhibitors; adenohypophyseal hormones; adrenergic neuron blocking agents; adrenocortical steroids; inhibitors of the biosynthesis of adrenocortical steroids; alpha-adrenergic agonists; alpha-adrenergic antagonists; selective alpha-two-adrenergic agonists; androgens; anti-addictive agents; antiandrogens; anti-infectives, such as antibiotics, antimicrobials, and antiviral agents; analgesics and analgesic combinations; anorexics; antihelmintics; antiarthritics; antiasthmatic agents; anticonvulsants; antidepressants; antidiabetic agents; antidiarrheals; antiemetic and prokinetic agents; antiepileptic agents; antiestrogens; antifungal agents; antihistamines; antiinflammatory agents; antimigraine preparations; anti-muscarinic agents; antinauseants; antineoplastics; antiparasitic agents; anti-parkinsonism drugs; antiplatelet agents; antiprogestins; antipruritics; antipsychotics; anti-pyretics; antispasmodics; anticholinergics; antithyroid agents; antitussives; azaspirodecane-diones; sympathomimetics; xanthine derivatives; cardiovascular preparations, including potassium and calcium channel blockers, alpha blockers, beta blockers, and antiarrhythmics; antihypertensives; diuretics and antidiuretics; vasodilators, including general coronary, peripheral, and cerebral; central nervous system stimulants; vasoconstrictors; cough and cold preparations, including decongestants; hormones, such as estradiol and other steroids, including cortico-steroids; hypnotics; immunosuppressives; muscle relaxants; parasympatholytics; psychostimulants; sedatives; tranquilizers; nicotine and acid addition salts thereof; benzodiazepines; barbituates; benzothiadiazides; beta-adrenergic agonists; beta-adrenergic antagonists; selective beta-one-adrenergic antagonists; selective beta-two-adrenergic antagonists; bile salts; agents affecting volume and composition of body fluids; butyrophenones; agents affecting calcification; catecholamines; cholinergic agonists; cholinesterase reactivators; dermatological agents; diphenylbutyl-piperidines; ergot alkaloids; ganglionic blocking agents; hydantoins; agents for control of gastric acidity and treatment of peptic ulcers; hematopoietic agents; histamines; 5-hydroxytryptamine antagonists; drugs for the treatment of hyperlipoproteinemia; laxatives; methylxanthines; moncamine oxidase inhibitors; neuronmuscular blocking agents; organic nitrates; pancreatic enzymes; phenothiazines; prostaglandins; retinoids; agents for spasticity and acute muscle spasms; succinimides; thioxanthines; thrombolytic agents; thyroid agents; inhibitors of tubular transport of organic compounds; drugs affecting uterine motility; vitamins; and the like; or a combination thereof.

Alternately or in addition to an opioid agonist, another active compound may be added including, but not limited to, fluorogestone acetate, hydroxyprogesterone, hydroxyprogesterone acetate, hydroxyprogesterone caproate, medroxyprogesterone acetate, norethindrone, norethindrone acetate, norethisterone, norethynodrel, desogestrel, 3-keto desogestrel, gestadene, levonorgestrel, estradiol, estradiol benzoate, estradiol valerate, estradiol cyprionate, estradiol decanoate, estradiol acetate, ethynyl estradiol, estriol, estrone, mestranol, betamethasone, betamethasone acetate, cortisone, hydrocortisone, hydrocortisone acetate, corticosterone, fluocinolone acetonide, prednisolone, prednisone, triamcinolone, aldosterone, androsterone, testosterone, methyl testosterone, or a combination thereof.

Alternately or in addition to an opioid agonist, another active compound may be added including, but not limited to: a) corticosteroids, e.g., cortisone, hydrocortisone, prednisolone, beclomethasone propionate, dexamethasone, betamethasone, flumethasone, triamcinolone, triamcinolone acetonide, fluocinolone, fluocinolone acetonide, fluocinolone acetate, clobetasol propionate, or the like, or a combination thereof; b) analgesic anti-inflammatory agents, e.g., acetaminophen, mefenamic acid, flufenamic acid, indomethacin, diclofenac, diclofenac sodium, alclofenac, ibufenac, oxyphenbutazone, phenylbutazone, ibuprofen, flurbiprofen, ketoprofen, salicylic acid, methylsalicylate, acetylsalicylic acid, 1-menthol, camphor, slindac, tolmetin sodium, naproxen, fenbufen, or the like, or a combination thereof; c) hypnotic sedatives, e.g., phenobarbital, amobarbital, cyclobarbital, lorazepam, haloperidol, or the like, or a combination thereof; d) tranquilizers, e.g., fulphenazine, thioridazine, diazepam, flurazepam, chlorpromazine, or the like, or a combination thereof; e) anti-hypertensives, e.g., clonidine, clonidine hydrochloride, bopinidol, timolol, pindolol, propranolol, propranolol hydrochloride, bupranolol, indenolol, bucumolol, nifedipine, bunitrolol, or the like, or a combination thereof; f) hypotensive diuretics, e.g., bendroflumethiazide, poly-thiazide, methylchlorthiazide, trichlor-methiazide, cyclopenthiazide, benzyl hydrochloro-thiazide, hydrochlorothiazide, bumetanide, or the like, or a combination thereof; g) anti-biotics, e.g., penicillin, tetracycline, oxytetracycline, metacycline, doxycycline, minocycline, fradiomycin sulfate, erythromycin, chloramphenicol, or the like, or a combination thereof; h) anesthetics, e.g., lidocaine, benzocaine, ethylaminobenzoate, or the like, or a combination thereof; i) antimicrobial agents, e.g., benzalkonium chloride, nitrofurazone, nystatin, sulfacet-amide, clotriamazole, or the like, or a combination thereof; j) anti-fungal agents, e.g., penta mycin, amphotericin B, pyrrol nitrin, clotrimazole, or the like, or a combination thereof; k) vitamins, e.g., vitamin A, ergocalciferol, cholecalciferol, octotriamine, riboflavin butyric acid ester, or the like, or a combination thereof; l) antiepileptics, e.g., nitrazepam, meprobamate, clonazepam, or the like, or a combination thereof; m) antihistamines, e.g., diphenhydramine hydrochloride, chlorpheniramine, diphenylimiclazole, or the like, or a combination thereof; n) antitussives, e.g., dextromethorphan, terbutaline, ephedrine, ephedrine hydrochloride, or the like, or a combination thereof; o) sex hormones, e.g., progesterone, estradiol, estriol, estrone, or the like, or a combination thereof; p) antidepressants, e.g., doxepin; q) vaso-dilators, e.g., nitroglycerin, isosorbide nitrate, nitroglycol, pentaerythritol tetranitrate, dipyridamole, or the like, or a combination thereof; r) other drugs, e.g., 5-fluorouracil, dihydroergotamine, desmopressin, digoxin, methoclopramide, domperidone, scopolamine, scopolamine hydrochloride, or the like, or a combination thereof; or the like; or a combination thereof.

In another embodiment, the active agent can include, but is not limited to, anti-staphylococcal agents (e.g., YSPXTNF [SEQ ID NO: 2], YSPWTNF [SEQ ID NO: 3], YSPWTNF-NH2 [SEQ ID NO: 4], GENBANK/AF202641 [SEQ ID NO: 5], GENBANK/AF205220 [SEQ ID NO: 6], GENBANK/AAG03056 [SEQ ID NO: 7], or the like, or combinations thereof). Other agents that modulate the production or secretion of bacterial or microbial toxins or virulence factors may also be used as active agents. For instance, thiolactones and bacterial toxin regulatory proteins such as RNAIII-inhibiting peptides (RIPs) are classes of active agents. See, e.g., Balaban, N., et al., "Regulation of *Staphylococcus aureus* pathogenesis via target of RNAIII-activating Protein (TRAP)," J. Biol Chem., 2001 Jan. 26; 276(4): 2658-67, which is incorporated by reference herein in its entirety.

When an active agent of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. In one embodiment, the salt includes ammonium, calcium, magnesium, potassium, or a sodium salt. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethylaminoethanol, ethanolamine, ethylene-diamine, N-ethylmorpholine, N-ethylpiperidine, glucamine, glucosamine, histidine, iso-propylamine, lysine, methyl-glucosamine, morpholine, piperazine, piperidine, polyamine resins, procaine, purine, theobromine, triethylamine, trimethylamine, tripropylamine, etc.

When an active agent of the present invention is basic, salts may be prepared from pharmaceutically acceptable non-toxic acids. Such acids include acetic, benzene-sulfonic, benzoic, camphorsulfonic, citric, ethane-sulfonic, fumaric, gluconic, glutamic, hydrobromic, hydrochloric, isethionic, lactic, maleic, mandelic, methane-sulfonic, mucic, nitric, pamoic, pantothenic, phosphoric, succinic, sulfuric, tartaric, p-toluenesulfonic, etc. In one embodiment, the acid includes citric, hydrobromic, maleic, phosphoric, sulfuric, and/or tartaric acids.

Although some active agents can be bound directly to the polymer surface of a substrate by the organometallic layer according to the invention, many active agents according to the present invention can often be attached to the polymer surface of a substrate via a codi-functional linkers or spacers bound to the organic overlayer. Such spaces or linkers will often be tailored to the particular active agent(s) used. It is noted that the a- and co functional groups of the linkers/spacers can be similar or different, and often are different particularly where release of the active agent(s) is(are) intended (e.g., in vivo). Such attachment (and release) of active agents can be effected by covalent bonding (cleaving), ionic bonding (dissociation), physical transitions of state such as crystallization (melting) or liquid crystalline-type ordering (disordering), hydrogen bonding (dissociation), van der Waals interactions (repulsions), or the like, or any combination thereof. The linkers/spacers can be of relatively small molecular weight (e.g., less than about 200 g/mol), relatively intermediate molecular weight (e.g., from about 200 to about 2000 g/mol), relatively large molecular weight (e.g., more than about 2000 g/mol), or some combination thereof. Particularly when the linkers/spacers are of relatively intermediate and/or relatively large molecular weight, they can include, but are not limited to, oligomers, polymers, and/or copolymers described above as bioactive moieties or biodegrade-able polymers; additionally or alternately, the linkers/spacers can include, but are not limited to, oligomers, polymers, and/or copolymers having one or more of the following types of repeat units: urethanes, ureas, ethers, ketones, esters, amines, carbonates, amides, saccharides, or the like, or combinations thereof.

In other embodiments, polyfunctional linkers/spacers can be used to attach active agents to the coatings/derivatized surfaces according to the invention. Such poly-functional linkers/spacers can include, but are not limited to, oligomers, polymers, and/or copolymers that are branched, hyper-branched, dendritic, star-shaped, brushes, combs, block, multiblock, or the like, or any combination thereof.

The transition metal phosphate esters can also serve as a template for first chemical, then biological growth of bone tissue hydroxyapatite in the implant surface. Surface-bound transition metal phosphate layers insinuate themselves directly into bone tissue hydroxylapatite to make a strong composite seal between the implant surface and the hydroxyapatite. Alternatively, the phosphate may be hydrolyzed to form transition metal polyphosphates having a two-dimensional structure, the layers of which also insinuate themselves directly into bone tissue hydroxyapatite.

Essentially any organophosphonic acid capable of forming a thin film on an organo-metallic surface is suitable for use with the present invention. The organophosphonic acid will have a hydrocarbon ligand that may be saturated or unsaturated, branched or unbranched, substituted or unsubstituted, and may be aromatic or non-aromatic. Typical hydrocarbon ligands of organophosphonic acids will contain between two and twenty carbon atoms or for example, between three and eighteen carbon atoms. Stearyl ligands, for example, may be used.

A preferred class of organophosphorus and organic carboxylic acids are those with omega-functionalized organo groups that can be chemically transformed to react and covalently bond to the aforementioned biologically active and pharmaceutically active compounds. Examples of such omega functional groups include amino, carboxylate, thiol, hydroxyl, carbonate, ester, carbamate, and amide groups.

A preferred application technique involves a two-stage vapor deposition process in which the transition metal alkoxide—or dialkylamide—is first vapor deposited on the polymer surface. When the reaction is complete, vacuum is applied to remove excess transition metal alkoxide and dialkylamine or alkanol by-product, which is then followed by vapor deposition of the organic overlayer material. Upon completion of the reaction with the organic compound, the vacuum is then applied to withdraw excess organic compound solution and alkanol or dialkylamine byproduct.

Suitable substrates with polymer surfaces also include fabrics formed from a woven or non-woven fiber. The fiber can be a natural fiber with exposed functional groups, such as silk, wool, cotton, collagen, linen, and the like. The fiber can also be a synthetic fiber with exposed amide groups, such as nylon.

The polymer-coated and polymer-cast substrates of the present invention may be fabricated into scaffolds for tissue engineering and tissue guided regeneration applications, including reconstructive surgery. The scaffolds may also be molded to form external scaffolding for the support of in vitro culturing of cells for the creation of external support organs. The scaffolds may also be used in transplantation as a matrix for dissociated cells.

Polymer scaffolds and mixed polymer/ceramic scaffolds for tissue engineering and their manufacture are known to those skilled in the art. The scaffold structure is typically porous to allow generous cellular ingrowth. The polymer scaffolds may also be molded to form external scaffolding for the support of in vitro culturing of cells for the creation of external support organs.

Polymers that are suitable for use as scaffold materials are non-toxic, physiologically compatible, and optionally biodegradable. The polymer must be selected for biocompatibility at the time of implant, and, if biodegradable, the products of its degradation process must also be biocompatible. Additional parameters that play an important role include the mechanical properties of the material, especially its mechanical rigidity. Relatively high rigidity is advantageous so that the scaffold can withstand the contractile forces exerted by cells growing within the scaffold. Also important are the thermal properties, such as the glass transition temperature, Tg, and the biodegradation kinetics, if degradable, which should match the rate of the healing process.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support. The scaffold polymer preferably degrades as the need for an artificial support diminishes.

In the reconstruction of structural tissues like cartilage and bone, tissue shape is integral to function, requiring the molding of the polymer scaffold into articles of varying thickness and shape. Any crevices, apertures or refinements desired in the three dimensional structure can be created by removing portions of the matrix with scissors, a scalpel, a laser beam or any other cutting instrument. Scaffold applications include the regeneration of tissues such as nervous, musculoskeletal, cartilaginous, tendenous, hepatic, pancreatic, ocular, integumentary, arteriovenous, urinary or any other tissue forming solid or hollow organs.

The scaffold may also be used in transplantation as a matrix for dissociated cells such as chondrocytes or hepatocytes to create a three-dimensional tissue or organ. Any type of cell can be added to the scaffold for culturing and implantation, including cells of the muscular and skeletal systems, such as mesenchymal stem cells, chondrocytes, fibroblasts, osteocytes and osteoblasts, parenchymal cells such as hepatocytes, pancreatic cells (including Islet cells), cells of intestinal origin, and other cells such as exocrine cells, bile duct cells, parathyroid cells, thyroid cells, cells of the adrenal-hypothalmic-pituitary axis, heart muscle cells, kidney epithelial cells, kidney tubular cells, kidney basement membrane cells, nerve cells, neurons, blood vessel cells, endothelial cells, cells forming bone and cartilage, smooth muscle cells, skeletal muscle cells, ocular cells, integumentary cells, keratinocytes and skin cells, and, either as obtained from donors, embryonic and non-embryonic stem cells, established cell culture lines, including embryonic and non-embryonic stem cell culture lines, and either before or after genetic engineering. Pieces of tissue can also be used, which may provide a number of different cell types in the same structure.

The cells are obtained from a suitable donor, or the patient into which they are to be implanted, dissociated using standard techniques and seeded onto and into the scaffold. In vitro culturing optionally may be performed prior to implantation. Alternatively, the scaffold is implanted, allowed to vascularize, then cells are injected into the scaffold. Methods and reagents for culturing cells in vitro and implantation of a tissue scaffold are known to those skilled in the art. The polymer scaffolds can be utilized in vivo as tissue engineering and tissue guided regeneration scaffold in mammals such as primates, including humans, sheep, horses, cattle, pigs, dogs, cats, rats and mice, or in vitro.

The polymer-coated and polymer-cast substrates of the present invention may also be fabricated from biocompatible polymers into articles for medical implant applications. The organic ligand bonded to the article surface can be a biologically- or pharmaceutically-active compound having utility as a coating on a medical implant. The polymer-coated and polymer-cast articles are formed into shaped articles such as vascular grafts and stents, bone plates, sutures, implantable sensors, barriers for surgical adhesion prevention, implantable drug delivery devices and other therapeutic agent articles. The same issues related to toxicity and tissue compatibility for tissue scaffold polymers also apply to medical implant polymers.

The following non-limiting examples set forth hereinbelow illustrate certain aspects of the present invention. They are not to be considered limiting as to the scope and nature of the present invention. In the examples which follow, all parts are by weight.

EXAMPLES

Example 1

Preparation of RGD-Modified Nylon Substrate

Activated nylon surface 4 was prepared by first casting films of 3 (Nylon 6/6; (R=$(CH_2)_4$CO; R'=$(CH_2)_6$NH) from 0.1 mM formic acid solution on glass microscope slides that were rinsed copiously in Millipore® water, and evacuated at $10^{-2}$ torr for 3 hours. The coated slides were then placed in a deposition chamber that was equipped with two stopcocks for exposure either to vacuum or to vapor of zirconium tetra(tert-butoxide). The chamber was evacuated to $10^{-3}$ torr for 30 minutes, and slides of 3 were exposed to vapor of zirconium tetra(tert-butoxide) (with external evacuation) for 30 seconds followed by 5 min exposure without external evacuation. This cycle was repeated twice, then followed by an additional 10 minutes of exposure without external evacuation. The chamber was then evacuated for 16 hours at $10^{-3}$ torr to ensure removal of excess zirconium tetra(tert-butoxide). The IR spectrum of polymer surface-bound Zr complex (4) showed $v_{C-H}$=2976 cm$^{-1}$, indicative of tert-butoxide groups.

Figure 2:
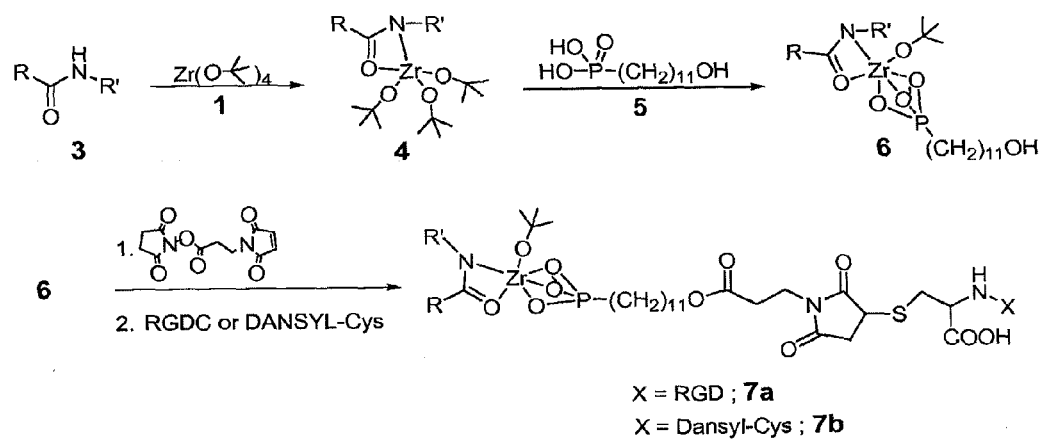
FIG. 2 depicts the reaction of nylon-Zr-amide complex with a phosphonic acid and RGDC [SEQ ID NO: 1] coupling.

RGD-modified nylon 7a was prepared by immersing a 4-coated slide in a 0.1 mM solution of phosphonoundecanol (5) in dry THF for 15 min to yield complex 6. Treatment of 6 in a 0.1 mM solution of 3-maleimidopropionic acid N-hydroxysuccinimide ester for 24 hrs under dry $N_2$ was followed by copious rinsing successively in acetonitrile and Millipore® water and drying in vacuo. As depicted in FIG. 2, either an RGDC [SEQ ID NO: 1] or DANSYL-cys-tethered surface (7a or 7b) can be obtained via Michael addition, which results in a complex with a 1:1 ratio of Zr to RGDC [SEQ ID NO: 1] or DANSYL-Cys. IR analysis of 6 showed peaks in the aliphatic region ($v_{CH2,asym}$=2922 cm$^{-1}$; ($v_{CH2,asym}$=2851 cm$^{-1}$) characteristic of disordered alkyl chains. Immersion of 6 in a 0.1 mM aqueous solution of RGDC [SEQ ID NO: 1] at pH 6.5 for 24 hours produced 7a.

Example 2

Preparation of RGD-Modified Nylon Substrate

RGD-derivatized surface 9a (FIG. 3) was prepared by immersing a 4-coated slide in a 0.1 mM solution of 3-maleimidopropionic acid N-hydroxysuccinimide ester in dry acetonitrile for 16 hours to produce 8. Immersion of 8 in a 0.1 mM aqueous solution of RGDC [SEQ ID NO: 1] at pH 6.5 for 24 hours produced 9a. The nylon-Zr surface complex was derivatized with the succinimide ester of 3-maleimidopropionic acid directly by transesterification to produce 8, which can result in either an RGDC [SEQ ID NO: 1] or DANSYL-Cys-tethered surface (9a or 9b). Complexes 9a and 9b have a 1:2 ratio of zirconium to RGDC [SEQ ID NO: 1] or DANSYL-Cys, respectively.

Example 3

Preparation of DANSYL-Cys-Modified Nylon Substrate

Figure 3:
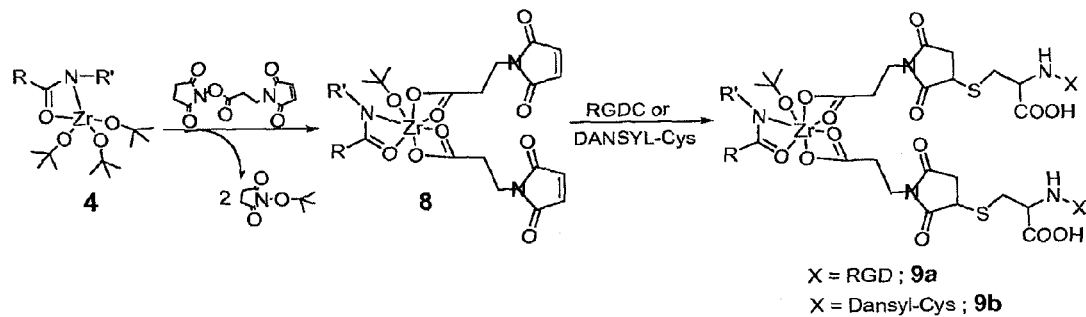
FIG. 3 depicts the transesterification reaction of nylon-Zr-amide complex and RGDC [SEQ ID NO: 1] coupling.

Fluorescent molecule-labeled analogues 7b and 9b were prepared as described for 7a and 9a, but a 0.1 mM aqueous solution of N-(5-(dimethylamino)-1-naphthyl-sulfonyl)-cysteine (DANSYL-Cys) was used instead of RGDC [SEQ ID NO: 1] (FIGS. 2 and 3).

To address the issue of solvent-induced polymer swelling, control films of 3 were prepared by soaking in 0.1 mM DANSYL-cys solution for 24 hrs. A calibration curve of fluorescence intensity versus concentration was measured for DANSYL-Cys solutions from 0.16 to 21 µM at pH 7.5 and pH 12.

Surface complex DANSYL content of 7b and 9b was quantified by immersion in water at pH 12 for 3 hours, which cleaves the Zr complexes from the surface, precipitates ZrO2, and releases fluorophore from 7b and 9b into solution. The amount of DANSYL surface-bound through Zr complexes 7b and 9b was measured to be 0.10 nmol/cm$^2$ and 0.18 nmol/cm$^2$, respectively. These amounts are consistent with the DANSYL:Zr stoichiometries of 1:1 and 2:1 indicated for 7b and 9b, respectively (FIGS. 2 and 3). Notably, they are at least an order of magnitude higher than the previously highest reported value of about 10 pmol/cm$^2$ for polymer surface-derivatization with a peptide. A substantial change in surface hydrophilicity was confirmed by a decrease in water contact angle (75° for 3 compared to 50° for 9a).

The approximate spatial surface coverage by RGD was calculated from its measured surface loading of 0.2 nmol/cm$^2$; assuming an RGD "footprint" of 40 Å$^2$ (determined using Chem 3D$^c$). This corresponds to coverage of about 0.4 cm$^2$ per cm$^2$ of surface, or 40%. Without being bound by theory, it is hypothesized that the percent surface coverage by the organic ligand depends upon the relative sizes of the organic ligand and the transition metal complex.

Example 4

Hydrolytic Stability of Modified Nylon Substrates

Nylon films (2 cm$^2$) derivatized as 7b and 9b and control films of 3 were immersed in water at pH 7.5 for 7 days at room temperature, and the supernatants were analyzed by fluorescence spectroscopy. The samples were then removed from solution, dried, and immersed in water at pH 12 for 3 hrs, after which the supernatants were again analyzed by fluorescence spectroscopy. Release of DANSYL groups was measured by fluorescence intensities of supernatants from treated 7b and 9b which were compared to the control sample (3) over this seven-day period. Unreacted DANSYLating reagent desorbed from the Nylon in about 3 hours. No release of surface-bound DANSYL material occurred over the next seven days.

Thus zirconium-amide surface-bound complexes are stable to hydrolysis under these conditions.

Example 5

Cell Response to Surface Modification

Cell responses to surfaces 3 and 9a were evaluated in vitro. NIH 3T3 cells were maintained in Dulbecco's Modified Eagle's Medium (DMEM) with 10% calf serum. Cells were washed with Phosphate-Buffered Saline (PBS) and released from tissue culture dishes using 50 mg/mL trypsin and 2 mg/mL EDTA in PBS. Trypsinization was stopped by washing cells in soybean trypsin inhibitor (Sigma). Cells were resuspended in serum-free DMEM at $5 \times 10^4$ cells/mL. Two milliliters of the cell suspension were added to wells containing the Nylon coated surfaces, which had been pre-blocked for 1 hr in 1% Bovine Serum Albumin After 90 minutes, non-adherent cells were removed and replaced with fresh, serum-free DMEM. Cells were fixed, permeabilized, and stained for the focal adhesion protein vinculin at the indicated time points.

Figures 4A, 4B, 4C:
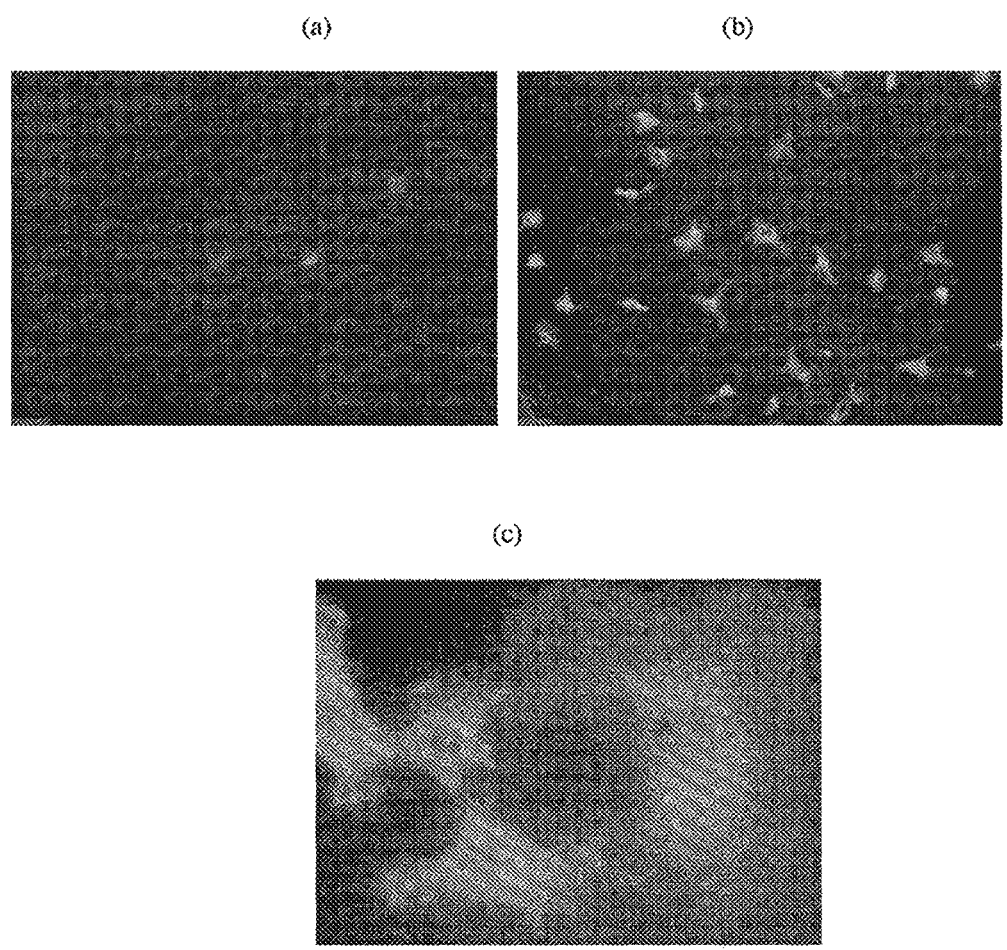
FIGS. 4a-4c depict fibroblast cell growth on surface embodiments of the invention according to one embodiment of a method of the invention.

Fibroblast cell spreading on (a) nylon 3 control at 3 hrs; (b) RGD-modified surface 9a at 3 hrs; and (c) RGD-modified surface 9a at 6 hrs is depicted in FIGS. 4a-4c. Staining shows vinculin, and scale bars are 50 microns. Compared to control untreated nylon (3), significant numbers of cells attached to the RGDC [SEQ ID NO: 1]-modified surface (9a). Cells were well spread on the RGD-modified surface showing many focal adhesions when stained with anti-vinculin antibodies, while the few cells on untreated nylon remained round.

Surface-bound Zr-amide complexes, which are readily synthesized on the surface of 20 Nylon 6/6, are thus effective for activation of that surface for further organic chemical transformation.

Example 6

Modification of Other Polymer Classes—Polyamide Control

The ability to modify polyurethanes, polyimides and polysulfonamides with a transition metal alkoxide with zirconium tetra(tert-butoxide) was evaluated on a small molecule model from which the ability to surface-modify the corresponding polymer can be readily predicted. As a control, the small molecule model was first tested for the polyamides of Examples 1-5 using N-hexylacetamide as the model.

Zr complex 2 (FIG. 1) was prepared by treating N-hexylacetamide (0.15 g, 1.0 mmol) with Zr tetra(tert-butoxide) 1 (0.40 g, 1.0 mmol) in dry $CH_2Cl_2$ for 1 hour under nitrogen. Solvent and reaction byproducts were removed in vacuo to yield Zr complex 2 in >95% yield as shown by $^1$H NMR ([CDCl3]: □ 0.8 (t, 3H); 1.3 (m, 35H); 1.9 (s, 3H); 3.2 (quartet, 2H)). The reaction proceeded via Zr coordination to the amide carbonyl, followed by N—H proton transfer to a tert-butoxide ligand, and loss of tert-butanol. The bonding for the amide moiety to Zr in 2 ($\eta^2$-coordination) is indicated by the 8 ppm downfield shift of the acyl carbon vs. the free amide ($^{13}$C NMR [CDCl3]: δ 170.1 for N-hexyl-acetamide; δ 178.1 for 2).

Examples 7-9

Modification of Other Polymer Classes

The N-hexylacetamide example was repeated in tetrahydrofuran (THF) at 20 C using methyl N-hexylcarbamate as a model for polyurethanes, succinimide as a model for polyimides, and N-hexyl p-toluene sulfonamide as a model for polysulfonamides. The reaction progress was observed via $^1$H NMR and reaction completion was calculated from the reduction in relative integration of the N—H NMR peak in each molecule. All reactions were assumed to proceed via zirconium complex coordination to "carbonyl" oxygen, N—H proton transfer to ligand, and loss of ligand.

The succinimide and N-hexyl p-toluene sulfonamide yields were about 90% after 30 minutes. The methyl N-hexyl carbamate yield was about 40% after three hours using a stoichiometric excess of zirconium alkoxide. This is evidence of the ability of transition metal alkoxides or amides to surface-modify the polymers.

Example 10

Polyurea Modification

Examples 7-9 were repeated using dicyclohexylurea as a model for polyurea and tetrakis(diethylamino)zirconium (IV) as the transition metal alkoxide. The yield was about 90% after 30 minutes. This is indicative of the ability of transition metal alkoxides or dialkylamides to surface-modify this polymer.

Example 11

Surface Reaction of Collagen with Zirconium Tetra(tert-butoxide)

Films of type 1 collagen (from bovine achilles tendon, Aldrich) were cast from a 0.1M solution in formic acid on glass microscope slides that were sonicated in ethanol, rinsed copiously in Millipore water, and evacuated at $10^{-1}$ torr for 3 h. The coated slides were then soaked for 24 hours in Millipore water, and baked at 110° C. for 16 hours to dehydrate them. These collagen slides were placed in a deposition chamber equipped with two stopcocks for exposure either to vacuum or to vapor of zirconium tetra(tert-butoxide). The chamber was evacuated to $10^{-3}$ torr for 30 min, and slides of collagen were exposed to vapor of Zr tetra(tert-butoxide) (with external evacuation) for 30 sec followed by 5 min exposure without external evacuation. This cycle was repeated twice and was then followed by an additional 30 min exposure without external evacuation. The chamber was then evacuated to $10^{-3}$ torr for 1 h to ensure removal of excess of zirconium tetra(tert-butoxide), and to give Zr-activated collagen.

Example 12

1,12-Diphosphonododecane-Modified Collagen

Collagen was derivatized with 1,12-diphosphonododecane by immersing a Zr-activated collagen slide in a 0.1 mM solution of 1,12-diphosphonododecane in dry THF for 1 h. The surface was rinsed copiously in dry THF to produce 1,12-diphosphonododecane-derivatized collagen.

Example 13

11-hydroxyundecylphosphonate-Modified Collagen

Collagen was derivatized with 11-hydroxyundecylphosphonate by immersing a Zr-activated collagen slide in a 0.1 mM solution of 11-hydroxyundecylphosphonate in dry THF for 1 h. This surface was rinsed copiously in dry THF to produce 11-hydroxyundecylphosphonate-derivatized collagen.

Example 14

RGD-Modified Collagen

RGD-derivatized collagen was prepared by immersing a Zr-activated collagen slide in a 0.1 mM solution of 3-maleimidopropionic acid in dry acetonitrile for 1 h to derivatize the collagen surface with maleimido groups. Immersion of this maleimido-derivatized collagen in a 0.1 mM aqueous solution of RGDC [SEQ ID NO: 1] at pH 6.5 for 24 h gave RGD-derivatized collagen.

Example 15

Cell Response to Collagen Surface Modification

Cellular response to collagen coated glass slides modified with various compounds was assessed by assaying adhesion to modified and control slides. Collagen coated slides were modified with 1,12-diphosphonododecane, 11-hydroxyundecylphosphonate and RGD according to the procedures in Examples 12-14. Bare glass slides and unmodified collagen coated glass slides were used as negative controls. Glass slides coated with the cell binding protein fibronectin were used as positive controls. Gasket sealed tissue culture chambers were affixed to each slide type and adhesion of human osteoblasts was assayed after 2 and 24 hour incubation periods using a Vybrant Cell Adhesion Assay Kit (invitrogen-V-13181). Representative data is shown in the table below.

| Slide Type | Percent Adhesion |
| --- | --- |
| Glass slide (−control) | 23.8% |
| Collagen coated glass slide (−control) | 41.1% |
| Collagen + 11-hydroxyundecylphosphonate | 60.9% |
| Collagen + 1,12-diphosphonododecane | 82.9% |
| Collagen + RGD | 90.8% |
| Fibronectin coated slide (+control) | 94.9% |

What is claimed is:

1. A coated substrate comprising (a) a substrate comprising a polymer surface wherein the polymer is selected from the group consisting of polyamides, polyacrylamides, polyimides, polyurethanes, polyureas, polyamines, polyepoxides, polyesters, polysaccharides, polyethers, polyketones, polysulfonamides, polysulfides and copolymers of two or more thereof; (b) an organometallic coating bonded to said polymer surface comprising a polyalkoxide or a polydialkylamide of transition metal atoms selected from the group consisting of atoms of Group 4, Group 5 and Group 6 of the Periodic Chart; and (c) an organophosphorus, organocarboxylic acid or organocarboxylic acid ester compound overlayer coated on and covalently bonded to said organometallic layer.

2. The coated substrate of claim 1, wherein the organo group of the organophosphorus, organocarboxylic acid or organocarboxylic acid ester overlayer compound is a saturated or unsaturated, substituted or unsubstituted alkyl group.

3. The coated substrate of claim 2, wherein said alkyl group is substituted in the omega position and the omega-substituents of the omega-substituted organophosphorus, organocarboxylic acid or organocarboxylic acid ester overlayer compounds are selected from the group consisting of carboxylate, carbamate, hydroxyl, keto, ether, oxy, carbonate, amino, amide and thiol.

4. The coated substrate of claim 2, further comprising a second overlayer of a biologically or pharmaceutically active compound covalently bonded to said organophosphorus, organocarboxylic acid or organocarboxylic acid ester compound overlayer.

5. The coated substrate of claim 1, wherein said overlayer comprises an organophosphorus compound selected from the group consisting of phosphoric acids, phosphonic acids and phosphinic acids.

6. The coated substrate of claim 5, wherein said organophosphorus overlayer comprises an organophosphoric acid compound or mixture of compounds of the structure:

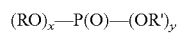

wherein x is 1 or 2, y is 1 or 2 and x+y=3; R is a radical having a total of 1-30 carbons; where R' is H, a metal or lower alkyl having 1-4 carbons; and, for at least a portion of the organo-phosphorus compounds in the overlayer, R' is H.

7. The coated substrate of claim 5, wherein said organophosphorus overlayer comprises an organophosphonic acid compound or mixture of compounds of the structure:

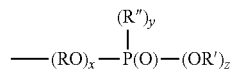

wherein x is 0 or 1, y is 1, z is 1 or 2 and x+y+z is 3; R and R" are each independently radicals having a total of 1 to 30 carbons; R' is H, a metal or lower alkyl having 1-4 carbons, and, for at least a portion of the organophosphorus compounds in the overlayer, R' is H.

8. The coated substrate of claim 5, wherein said organophosphorus overlayer comprises an organophosphinic acid compound or mixture of compounds of the structure:

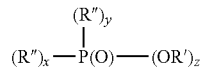

wherein x is 0, 1 or 2, y is 0, 1 or 2, z is 1 and x+y+z is 3; R and R" are each independently radicals having a total of 1 to 30 carbons; R' is H, a metal or lower alkyl and, for at least a portion of the organophosphorus compounds in the overlayer, R' is H.

9. The coated substrate of claim 1, wherein said overlayer comprises an organophosphorus or organocarboxylic acid compound with an organo group containing a $C_6$ to $C_{18}$ hydrocarbon or substituted hydrocarbon group.

10. The coated substrate of claim 1, wherein the substrate is a molded polymer article.

11. The coated substrate of claim 1, wherein the polymer is in the form of a coating.

12. The coated substrate of claim 11, wherein the polymer is a coating on an article made from another material selected from the group consisting of glass, silicon dioxide, metal, and another polymer.

13. The coated substrate of claim 1, wherein said overlayer comprises a biologically or pharmaceutically active compound covalently bonded to the organometallic coating layer.

14. The coated substrate of claim 1, wherein said overlayer comprises a biologically active ligand compound selected from cell attachment mediators or a substance selected from the group consisting of osteoinductive substances and substances that induce cellular growth, proliferation, and/or differentiation.

15. The coated substrate of claim 14, wherein said biologically active ligand compound is selected from the group consisting of osteoinductive substances and substances that induce cellular growth and proliferation and integrin cell attachment mediators.

16. The coated substrate of claim 15, wherein said biologically active ligand compound is selected from the group consisting of bone morphogenic proteins (BMP), epidermal growth factor (EGF), fibroblast growth factor (FGF), platelet-derived growth factor (PDGF), insulin-like growth factor (IGF-I and II), TGF-β and vascular endothelial growth factor (VEGF).

17. The coated substrate of claim 14, wherein said osteoinductive substances comprise bone morphogenic proteins (BMP), and said substances that induce cellular growth comprise epidermal growth factor (EGF), fibroblast growth factor (FGF), platelet-derived growth factor (PDGF), insulin-like growth factor (IGF-I and II), TGF-β, and vascular endothelial growth factor (VEGF).

18. The coated substrate of claim 1, wherein said overlayer comprises a pharmaceutically active compound selected from the group consisting of anti-neoplastic and anti-proliferative agents.

19. The coated substrate of claim 1, wherein said overlayer comprises a active agent selected from the group consisting of acyclovir, cephradine, malphalen, tamoxifen, raloxifene, daunomycin, adriamycin, plumbagin, chlorambucil, ephedrine, atropine, quinine, digoxin, quinidine, biologically active peptides, chlorin $e_6$, cephalothin, proline, proline analogues, penicillin V, aspirin, ibuprofen, steroids and nicotinic acid.

20. A polymer scaffold for tissue engineering comprising the coated substrate of claim 1.

21. A polymer scaffold for tissue engineering comprising the coated substrate of claim 1, wherein said overlayer comprises a biologically active ligand for cellular or tissue ingrowth.

22. The polymer scaffold of claim 21, wherein said scaffold is adapted for the re-generation of nervous, musculo-skeletal, cartilaginous, tendenous, hepatic, pancreatic, ocular, integumentary, arterio-venous or urinary tissues or tissues forming solid or hollow organs.

23. The polymer scaffold of claim 21, containing cells selected from the group consisting of cells of the muscular and skeletal systems, parenchymal cells, cells of intestinal origin, exocrine cells, bile duct cells, parathyroid cells, thyroid cells, cells of the adrenal-hypothalmic-pituitary axis, heart muscle cells, kidney epithelial cells, kidney tubular cells, kidney basement membrane cells, nerve cells, blood vessel cells, cells forming bone and cartilage, smooth muscle cells, skeletal muscle cells, ocular cells, integumentary cells, keratinocytes, skin cells and endothelial cells.

24. The polymer scaffold of claim 21, wherein said cells are selected from the group consisting of chondrocytes, fibroblasts, osteocytes, osteoblasts, hepatocytes and pancreatic cells.

25. The polymer scaffold of claim 21, containing cells selected from the group consisting of cells obtained from donors, embryonic stem cells, non-embryonic stem cells, cells from established cell culture lines, cells before genetic engineering and cells after genetic engineering.

26. An implantable medical device characterized by one or more surfaces comprising the coated substrate of claim 1.

27. A method of regulating cellular attachment, migration and proliferation on a polymeric substrate, characterized by contacting living cells, tissues or biological fluids containing living cells with the polymer scaffold of claim 21.

* * * * *